US006933091B2

(12) United States Patent
Sekine et al.

(10) Patent No.: US 6,933,091 B2
(45) Date of Patent: *Aug. 23, 2005

(54) PHOTOCONDUCTOR FOR ELECTROPHOTOGRAPHY AND QUINOMETHANE COMPOUND

(75) Inventors: Nobuyuki Sekine, Kanagawa (JP); Masami Kuroda, Kanagawa (JP); Yoshihiro Ueno, Nagano (JP); Kenichi Ohkura, Nagano (JP)

(73) Assignee: Fuji Electric Imaging Devices Co., Ltd., Nagano (JP)

( * ) Notice: Subject to any disclaimer, the term of this patent is extended or adjusted under 35 U.S.C. 154(b) by 103 days.

This patent is subject to a terminal disclaimer.

(21) Appl. No.: 10/444,094

(22) Filed: May 23, 2003

(65) Prior Publication Data

US 2004/0033430 A1 Feb. 19, 2004

(30) Foreign Application Priority Data

May 28, 2002 (JP) ........................................ 2002-154097
Apr. 9, 2003 (JP) ........................................ 2003-105039

(51) Int. Cl.$^7$ ........................ G03G 5/04; C07D 307/02; C07D 405/02

(52) U.S. Cl. ........................ 430/76; 399/159; 549/472; 549/497

(58) Field of Search ........................ 430/76, 75, 58.05; 399/159; 549/472, 497

(56) References Cited

U.S. PATENT DOCUMENTS 5,424,158 A * 6/1995 Murakami et al. ............ 430/83

FOREIGN PATENT DOCUMENTS

| | | |
|---|---|---|
| JP | 01-206349 | 8/1989 |
| JP | 01-230054 | 9/1989 |
| JP | 03-290666 | 12/1991 |
| JP | 04-338760 | 11/1992 |
| JP | 04-360148 | 12/1992 |
| JP | 05-092936 | 4/1993 |
| JP | 05-150481 | 6/1993 |
| JP | 05-279582 | 10/1993 |
| JP | 06-059483 | 3/1994 |
| JP | 06-130688 | 5/1994 |
| JP | 07-179775 | 7/1995 |
| JP | 08-278643 | 10/1996 |
| JP | 09-151157 | 6/1997 |
| JP | 09-190002 | 7/1997 |
| JP | 09-190003 | 7/1997 |
| JP | 09-281728 | 10/1997 |
| JP | 09-281729 | 10/1997 |
| JP | 10-073937 | 3/1998 |
| JP | 10-239874 | 9/1998 |
| JP | 2000-075520 | 3/2000 |
| JP | 2000-143607 | 5/2000 |
| JP | 2000-199979 | 7/2000 |
| JP | 2001-142239 | 5/2001 |
| JP | 2001-222122 | 8/2001 |
| JP | 2002-037755 | 2/2002 |

OTHER PUBLICATIONS

Yasufumi Mizuta et al., Synthesis and Xerographic Properties of Novel Naphthoquinone, Japan Hardcopy '97, pp. 21–24.

Yasuhiro Yamaguchi et al., Application of Unsymmetrical Diphenoquinone Derivatives to Xerography (1) Molecular Design of a Novel Class of Polymer–dispersable Electron–transport–active Compounds Jul. 2, 1991, pp. 266–273.

Yutaka Ohmori, "Recent Development of Highly Efficient Organic EL Materials," Japan Journal of Applied Physics, Oyo Buturi, vol. 70, No. 12, pp. 1419–1425 (2001).

* cited by examiner

*Primary Examiner*—John L Goodrow

(57) ABSTRACT

A highly sensitive positively charged type electrophotographic photoconductor includes an organic compound that transports electrons efficiently, improving light emission efficiency. The photoconductor is used in an electrophotographic drum, an electrophotographic cartridge and an electrophotographic apparatus. The photosensitive layer includes at least one compound represented by the following general formula (I)

(I)

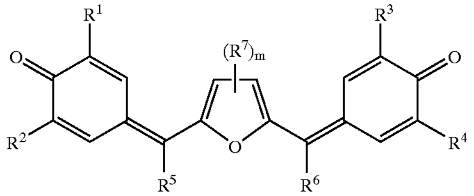

wherein each of $R^1$, $R^2$, $R^3$ and $R^4$, is independently selected from the group consisting of hydrogen atoms, alkyl groups having 1–6 carbon atoms that optionally have substituents and aryl groups that optionally have substituents, each of $R^5$ and $R^6$ is independently selected from the group consisting of hydrogen atoms, alkyl groups having 1–6 carbon atoms that optionally have substituents, aryl groups that optionally have substituents and heterocyclic groups that optionally have substituents, $R^7$ is selected from the group consisting of halogen atoms, alkyl groups having 1–6 carbon atoms that optionally have substituents, aryl groups that optionally have substituents and heterocyclic groups that optionally have substituents, m represents an integer of 0 to 2 and a plurality of $R^7$s are the same or different, the substituents being selected from a group consisting of halogen atoms, alkyl groups having 1–6 carbon atoms, alkoxy groups having 1–6 carbon atoms, aryl groups, and heterocyclic groups.

8 Claims, 6 Drawing Sheets

PHOTOCONDUCTOR FOR ELECTROPHOTOGRAPHY AND QUINOMETHANE COMPOUND

CROSS-REFERENCE TO RELATED APPLICATIONS

This application claims the benefit of Japanese Application No. PA 2002-154097, filed May 28, 2002, and Japanese Application No. PA 2003-105039, filed Apr. 9, 2003, in the Japanese Intellectual Property Office, the disclosures of which are incorporated herein by reference.

BACKGROUND OF THE INVENTION

1. Field of the Invention

The present invention relates to a photoconductor for electrophotography (hereinafter also referred to simply as "a photoconductor"), and in particular, to a photoconductor for electrophotography provided with a photosensitive layer that includes organic material on a conductive substrate, and that is used for a printer, a copy machine and the like of an electrophotographic system.

Furthermore, the invention relates to a quinomethane compound, and in detail, to a new quinomethane compound that is useful as an electron transporting material in a photoconductor for electrophotography (hereinafter also referred to as "a photoconductor"), an organic electroluminescence (EL) device and the like.

2. Description of the Related Art

Previously, an inorganic photoconductive material such as selenium or selenium alloy, or a material with an inorganic photoconductive material such as zinc oxide or cadmium sulfide, dispersed in a resin binder, has been used as a photosensitive layer of a photoconductor for electrophotography. In recent years, studies of photoconductors for electrophotography using organic photoconductive materials have progressed to find practical uses for some of the materials with improved sensitivity and durability.

A photoconductor is required to hold surface charges in a dark place, generate charges by receiving light, and transport charges by similarly receiving light. Thus, a single layered photoconductor may provide such functions in one layer, and a layered photoconductor may include a plurality of layers, each layer having a separated function, e.g., a layer contributing mainly to charge generation, and a layer contributing to retention of surface charges in a dark place and transportation of the charges when receiving light.

For example, the Carlson system may be applied to image formation by electrophotography using such photoconductors. The image formation with the system is carried out by charging a photoconductor in a dark place by corona discharge, formation of electrostatic images such as characters and pictures of an original document on the surface of the charged photoconductor, development of the formed electrostatic images with toner, and fixing of the developed toner image onto a support, such as a piece of paper. After the toner image has been transferred, the photoconductor is subjected to erasure of the charge, removal of residual toner, and the like, so that the photoconductor may be used again thereafter.

Organic photoconductors being put to practical use have advantages in flexibility, film formability, low cost, safety and the like, compared with inorganic photoconductors. Furthermore, with a variety of materials, further improvements are made possible with respect to sensitivity, durability, and the like.

Most of the organic conductors are layered organic conductors in which each layer's functions are separate, e.g., have a charge generating layer and a charge transporting layer. In general, the layered organic photoconductor is provided with a charge generating layer and a charge transporting layer, formed in the order recited, on a conductive substrate. The charge generating layer includes a charge generating material, such as a pigment or a dye, and the charge transporting layer includes a charge transporting material, such as hydrazone or triphenylamine. Thus, the organic photoconductor, due to the electron donating property of the charge transporting material, becomes a hole-transport-type of layer that has sensitivity when the surface of the photoconductor is negatively charged. In the negatively charged type of layer, however, compared with a positively charged type of layer, the corona discharge used at charging is unstable. In addition, ozone, nitrogen oxides, and the like are generated, which are adsorbed on the photoconductor surface and may cause physical and chemical degradation. Furthermore, there is a concern about harming the environment. In such respects, a positively charged type photoconductor, having a higher degree of flexibility in service conditions than the negatively charged photoconductor, has a wider scope of application thereof, and is thus more advantageous.

Thus, a method is proposed to use the positively charged type photoconductor and put the photoconductor to practical use, wherein a charge generating material and a charge transporting material are dispersed in a resin binder at the same time to make a photosensitive layer used as a single layer. The single layered photoconductor, however, has a sensitivity that is insufficient for being applied to a high-speed machine, and also necessitates further improvement in repeating characteristics and the like.

In addition, to provide a layered structure of a function separation type that achieves high sensitivity, a method may form a photoconductor by layering a charge generating layer on a charge transporting layer to use the photoconductor as a positively charged type. With the method, however, since the charge generating layer is formed on the surface, there are problems in stability when the layer is repeatedly used, for example, problems due to corona discharge, light irradiation, mechanical wear, and the like. In this case, a protecting layer on the charge generating layer may be provided. Although the protecting layer improves the structure with respect to mechanical wear, degradation in electrical properties, such as sensitivity and the like, are not yet solved.

Furthermore, a method has been proposed for forming a photoconductor by layering a charge transporting layer having an electron transporting property on a charge generating layer.

For example, 2,4,7-trinitro-9-fluorenon and the like may be used as charge transporting materials having an electron transporting property. The materials, however, are carcinogenic, causing a safety problem. In addition to this, cyano compounds and quinone compounds have been proposed in Japanese Patent Publications such as JP-A-1-206349, JP-A-6-59483, JP-A-9-190002, JP-A-9-190003, and the like. However, no electron transport material has been obtained that is sufficient for practical use.

Further, a large number of electron transporting materials and photoconductors for electrophotography using the materials have become known, and are proposed and described in, for example, JP-A-4-360148, Journal of the Society of Electrophotography of Japan, Vol. 30, p. 266 to 273 (1991), JP-A-3-290666, JP-A-5-92936, Proceedings of Pan-Pacific Imaging Conference/Japan Hardcopy 1998, Jul. 15 to 17, 1998 JAHALL, Tokyo, Japan, p. 207 to 210 (1998), JP-A-9-151157, Proceedings of Japan Hardcopy 1997, Jul. 9, 10, 11, 1997, JAHALL (Otemachi, Tokyo), p. 21 to 24 (1997), JP-A-5-279582, JP-A-7-179775, Proceedings of Japan Hardcopy 1992, Jul. 6, 7, 8, 1992, JAHALL (Otemachi, Tokyo), p. 173 to 176 (1992), JP-A-10-73937, JP-A-4-338760, JP-A-1-230054, JP-A-8-278643, JP-A-2001-222122, and the like. Moreover, photoconductors, each using hole transporting materials and electron transporting materials in combination in a single layered photosensitive layer, are noted as being highly sensitive and have begun to be put to practical use. The photoconductors are described in, for example, JP-A-5-150481, JP-A-6-130688, JP-A-9-281728, JP-A-9-281729, JP-A-10-239874, and the like.

Furthermore, there are organic ELs implemented as light-emitting devices using organic photoconductive materials, which devices are expected to be applied to a display, and the like. With respect to the organic ELs, a number of proposals are being presented to improve organic materials, and some of the proposals are being put to practical use.

The simplest structure of the organic EL is a structure in which a light-emitting layer includes a light-emitting material as an organic compound held between the electrodes. A current flows in the electrodes, causing electrons and holes to be injected from the electrodes into the light-emitting layer, by which excitons are formed in the light-emitting layer to bring about a recombination that produces light-emission. Moreover, to efficiently inject electrons and holes from the electrodes into the light-emitting layer, and the like, a structure is also proposed in which functional layers, such as a hole transporting layer, a hole injecting layer, an electron transporting layer, and an electron injecting layer are layered together with a light-emitting layer. Of the layers, for the electron transporting layer and the electron injecting layer, organic compounds which have electron transporting functions are used (See Ohmori, "Recent development of highly efficient organic EL materials," OYO BUTURI, Vol.70, No.12, p. 1419 to 1425 (2001)).

SUMMARY OF THE INVENTION

Thus far, the inventors have proposed various photoconductors containing excellent electron transport materials (for example, descriptions in JP-A-2000-75520, JP-A-2000-199979, JP-A-2000-143607 and JP-A-2001-142239, and the like). However, recent demands for highly sensitive photoconductors require realization of photoconductors with high performances that use new charge transporting materials that have improved electron transporting ability.

Accordingly, it is an aspect of the present invention to provide a highly sensitive positively charged type photoconductor of a copy machine and a printer by using a new organic compound, not used previously, as an electron transporting material in the photosensitive layer.

Moreover, also in an application to an organic EL, high performance electron transporting materials provide higher brightness than previously attainable and improve light emission efficiency.

Accordingly, it is an aspect of the present invention to provide a compound having an excellent electron transporting function and that is useful for applications to a conductor for electrophotography and an organic EL.

In order to achieve the above aspects, there is provided a photoconductor for electrophotography. The photoconductor has a photosensitive layer comprising a charge generating material and a charge transporting material on a conductive substrate, wherein the photosensitive layer comprises at least one compound represented by the following general formula (I):

(I)

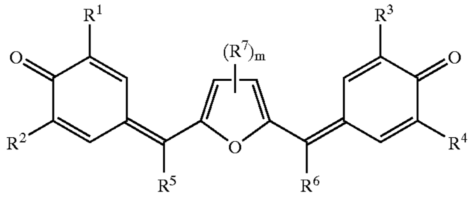

wherein each of $R^1$, $R^2$, $R^3$ and $R^4$, is independently selected from the group consisting of hydrogen atoms, alkyl groups having 1–6 carbon atoms that optionally have substituents and aryl groups that optionally have substituents, each of $R^5$ and $R^6$ is independently selected from the group consisting of hydrogen atoms, alkyl groups having 1–6 carbon atoms that optionally have substituents, aryl groups that optionally have substituents and heterocyclic groups that optionally have substituents, $R^7$ is selected from the group consisting of halogen atoms, alkyl groups having 1–6 carbon atoms that optionally have substituents, aryl groups that optionally have substituents and heterocyclic groups that optionally have substituents, m represents an integer of 0 to 2 and a plurality of $R^7$s are the same or different, the substituents being selected from a group consisting of halogen atoms, alkyl groups having 1–6 carbon atoms, alkoxy groups having 1–6 carbon atoms, aryl groups, and heterocyclic groups. The above-described photosensitive layer may be a single layered photosensitive layer. The photoconductor may also be utilized in an electrophotographic apparatus to carry out a charging process by a positive charging process.

In order to achieve aspects recited above, there is provided a quinomethane compound having a structure represented by the following general formula (I):

(I)

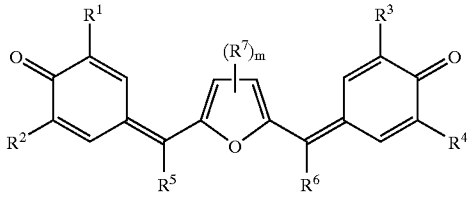

wherein each of $R^1$, $R^2$, $R^3$ and $R^4$, is independently selected from the group consisting of hydrogen atoms, alkyl groups having 1–6 carbon atoms that optionally have substituents and aryl groups that optionally have substituents, each of $R^5$ and $R^6$ is independently selected from the group consisting of hydrogen atoms, alkyl groups having 1–6 carbon atoms that optionally have substituents, aryl groups that optionally have substituents and heterocyclic groups that optionally have substituents, $R^7$ is selected from the group consisting of halogen atoms, alkyl groups having 1–6 carbon atoms that optionally have substituents, aryl groups that optionally have substituents and heterocyclic groups that optionally have substituents, m represents an integer of 0 to 2 and a plurality of $R^7$s are the same or different, the substituents being selected from a group consisting of halogen atoms, alkyl groups having 1–6 carbon atoms, alkoxy groups having 1–6 carbon atoms, aryl groups, and heterocyclic groups.

The photoconductor may also be utilized in an electrophotographic apparatus to carry out a charging process by a positive charging process.

In order to achieve the above aspects, there is provided an electrophotographic drum comprising a drum and an electrophotographic photoconductor on the drum, wherein the electrophotographic photoconductor comprises a photosensitive layer having a charge generating material and a charge transporting material on a conductive substrate, wherein the photosensitive layer comprises at least one compound represented by the following general formula (I):

(I)

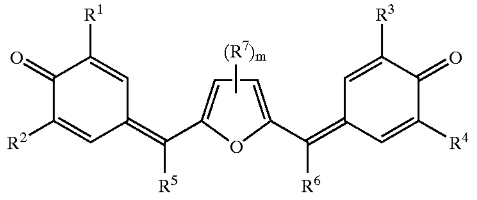

wherein each of $R^1$, $R^2$, $R^3$ and $R^4$, is independently selected from the group consisting of hydrogen atoms, alkyl groups having 1–6 carbon atoms that optionally have substituents and aryl groups that optionally have substituents, each of $R^5$ and $R^6$ is independently selected from the group consisting of hydrogen atoms, alkyl groups having 1–6 carbon atoms that optionally have substituents, aryl groups that optionally have substituents and heterocyclic groups that optionally have substituents, $R^7$ is selected from the group consisting of halogen atoms, alkyl groups having 1–6 carbon atoms that optionally have substituents, aryl groups that optionally have substituents and heterocyclic groups that optionally have substituents, m represents an integer of 0 to 2 and a plurality of $R^7$s are the same or different, the substituents being selected from a group consisting of halogen atoms, alkyl groups having 1–6 carbon atoms, alkoxy groups having 1–6 carbon atoms, aryl groups, and heterocyclic groups.

In order to achieve the above aspects, there is provided an electrophotographic cartridge comprising an electrophotographic photoconductor that includes a photosensitive layer having a charge generating material and a charge transporting material on a conductive substrate, wherein the photosensitive layer comprises at least one compound represented by the following general formula (I):

(I)

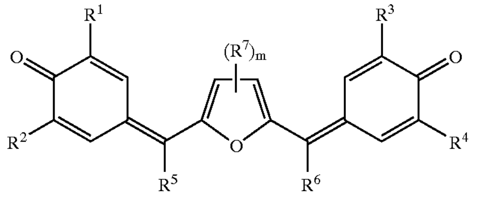

wherein each of $R^1$, $R^2$, $R^3$ and $R^4$, is independently selected from the group consisting of hydrogen atoms, alkyl groups having 1–6 carbon atoms that optionally have substituents and aryl groups that optionally have substituents, each of $R^5$ and $R^6$ is independently selected from the group consisting of hydrogen atoms, alkyl groups having 1–6 carbon atoms that optionally have substituents, aryl groups that optionally have substituents and heterocyclic groups that optionally have substituents, $R^7$ is selected from the group consisting of halogen atoms, alkyl groups having 1–6 carbon atoms that optionally have substituents, aryl groups that optionally have substituents and heterocyclic groups that optionally have substituents, m represents an integer of 0 to 2 and a plurality of $R^7$s are the same or different, the substituents being selected from a group consisting of halogen atoms, alkyl groups having 1–6 carbon atoms, alkoxy groups having 1–6 carbon atoms, aryl groups, and heterocyclic groups; and at least one of a charging device that charges the electrophotographic photoconductor; a developing device that develops an electrostatic latent image formed on the electrophotographic photoconductor; and a cleaning device which cleans a surface of the electrophotographic photoconductor, wherein the electrophotographic cartridge is attachable to and detachable from the electrophotographic apparatus.

In order to achieve the above aspects, there is provided an electrophotographic apparatus comprising: a photoconductor unit comprising an electrophotographic photoconductor that includes a photosensitive layer having a charge generating material and a charge transporting material on a conductive substrate, wherein the photosensitive layer comprises at least one compound represented by the following general formula (I):

(I)

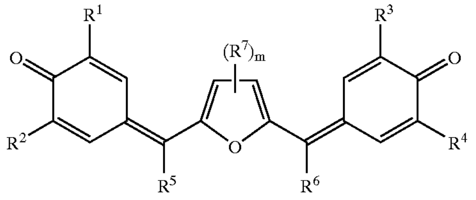

wherein each of $R^1$, $R^2$, $R^3$ and $R^4$, is independently selected from the group consisting of hydrogen atoms, alkyl groups having 1–6 carbon atoms that optionally have substituents and aryl groups that optionally have substituents, each of $R^5$ and $R^6$ is independently selected from the group consisting of hydrogen atoms, alkyl groups having 1–6 carbon atoms that optionally have substituents, aryl groups that optionally have substituents and heterocyclic groups that optionally have substituents, $R^7$ is selected from the group consisting of halogen atoms, alkyl groups having 1–6 carbon atoms that optionally have substituents, aryl groups that optionally have substituents and heterocyclic groups that optionally have substituents, m represents an integer of 0 to 2 and a plurality of $R^7$s are the same or different, the substituents being selected from a group consisting of halogen atoms, alkyl groups having 1–6 carbon atoms, alkoxy groups having 1–6 carbon atoms, aryl groups, and heterocyclic groups; and at least one of a charging device which charges the photoconductor; an imagewise light irradiating device/developing device which irradiates the charged photoconductor unit with imagewise light to form an electrostatic latent image on the photoconductor unit and develops the electrostatic latent image with a toner to form a toner image on the photoconductor unit; and a transfer device which transfers the toner image onto a receiving material.

Additional aspects and/or advantages of the invention will be set forth in part in the description which follows and, in part, will be obvious from the description, or may be learned by practice of the invention.

BRIEF DESCRIPTION OF THE DRAWINGS

These and other aspects and/or advantages of the invention will become apparent and more readily appreciated from the following description of the embodiments of the present invention, taken in conjunction with the accompanying drawings of which.

DETAILED DESCRIPTION OF THE PREFERRED EMBODIMENTS

Figure 1:
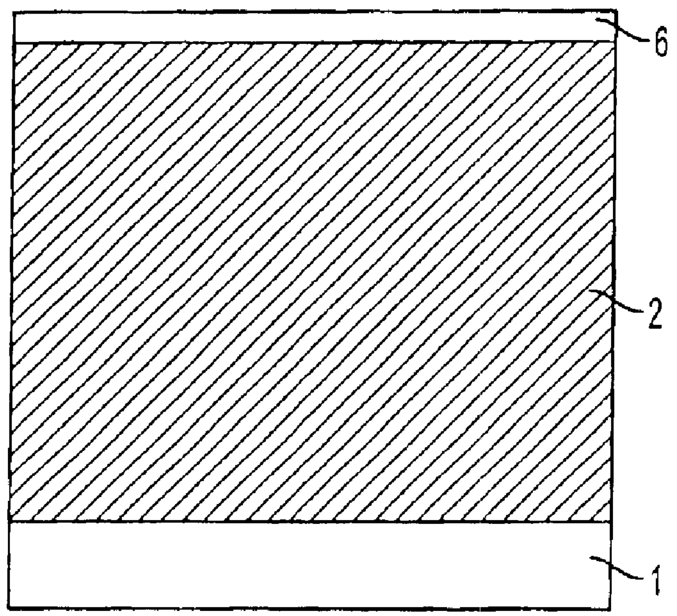
FIG. 1 is a schematic cross sectional view (not to scale) illustrating an example of a single layered photoconductor for electrophotography in accordance with an embodiment of the present invention.

Reference will now be made in detail to the embodiments of the present invention, examples of which are illustrated in the accompanying drawings, wherein like reference numerals refer to like elements throughout. The embodiments are described below in order to explain the present invention by referring to the figures.

The inventors have intensively studied various kinds of organic materials to achieve the above-described aspects. As a result, the inventors have found that, by using a specific compound expressed by the general formula (I) shown in the following and having an electron transporting property, a highly sensitive photoconductor is obtained, which may be used in a positively charged type photoconductor.

Namely, in order to solve the above-described problems, the photoconductor for electrophotography according to embodiments of the present invention is a photoconductor for electrophotography wherein a photosensitive layer containing a charge generating material and a charge transporting material is provided on a conductive substrate, and is characterized in that the photosensitive layer contains at least one kind of compound expressed by the following general formula (I):

(I)

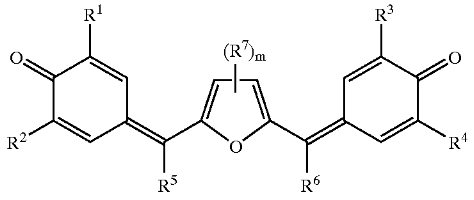

In the formula (I), $R^1$, $R^2$, $R^3$ and $R^4$, may be the same or different, i.e., are independently selected from the group consisting of hydrogen atoms, alkyl groups having 1–6 carbon atoms that optionally have substituents, aryl groups that optionally have substituents, $R^5$ and $R^6$ may be the same or different, i.e., each of $R^5$ and $R^6$ is independently selected from the group consisting of hydrogen atoms, alkyl groups having 1–6 carbon atoms that optionally have substituents, aryl groups that optionally have substituents and heterocyclic groups that optionally have substituents, $R^7$ is selected from the group consisting of halogen atoms, alkyl groups having 1–6 carbon atoms that optionally have substituents, aryl groups that optionally have substituents, and heterocyclic groups that optionally have substituents, m represents an integer of 0 to 2 and a plurality of $R^7$s may be the same or different. The substituents are independently selected from the group consisting of halogen atoms, alkyl groups having 1–6 carbon atoms, alkoxy groups having 1–6 carbon atoms, aryl groups, and heterocyclic groups.

Furthermore, in order to solve the above-described problems, the compound according to the invention is a quinomethane compound characterized by having a structure represented by the following general formula (I):

(I)

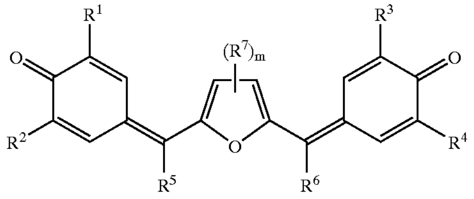

In the formula (I), $R^1$, $R^2$, $R^3$ and $R^4$, may be the same or different, i.e., are independently selected from the group consisting of hydrogen atoms, alkyl groups having 1–6 carbon atoms that optionally have substituents, aryl groups that optionally have substituents, $R^5$ and $R^6$ may be the same or different, i.e., each of $R^5$ and $R^6$ is independently selected from the group consisting of hydrogen atoms, alkyl groups having 1–6 carbon atoms that optionally have substituents, aryl groups that optionally have substituents and heterocyclic groups that optionally have substituents, $R^7$ is selected from the group consisting of halogen atoms, alkyl groups having 1–6 carbon atoms that optionally have substituents, aryl groups that optionally have substituents, and heterocyclic groups that optionally have substituents, m represents an integer of 0 to 2 and a plurality of $R^7$s may be the same or different. The substituents are independently selected from the group consisting of halogen atoms, alkyl groups having 1–6 carbon atoms, alkoxy groups having 1–6 carbon atoms, aryl groups, and heterocyclic groups.

Specific examples of the compounds expressed by the above-described general formula (I) are shown by the following structural formulas (I-1) to (I-59). In the invention, however, the compounds are not limited thereto. In the following specific examples, + represents t-butyl groups.

(I-1)

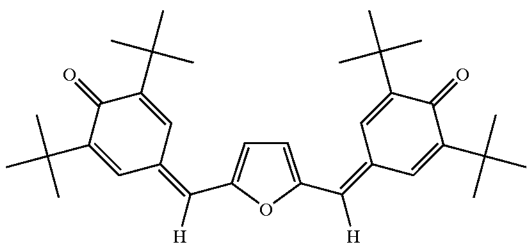

-continued
(I-2)
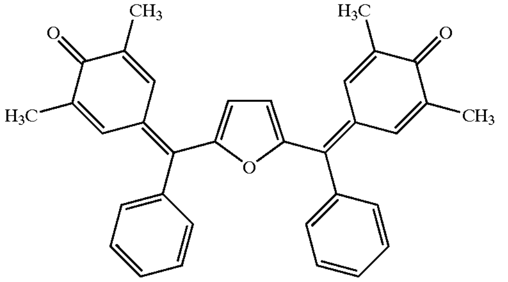
(I-3)
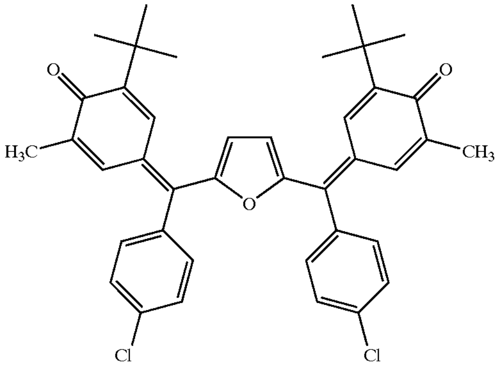
(I-4)
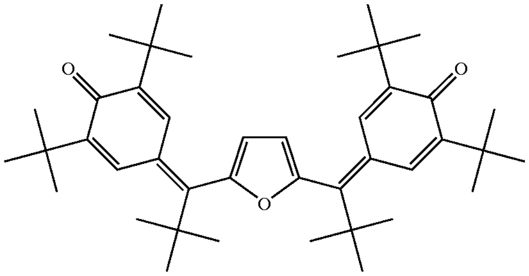
(I-5)
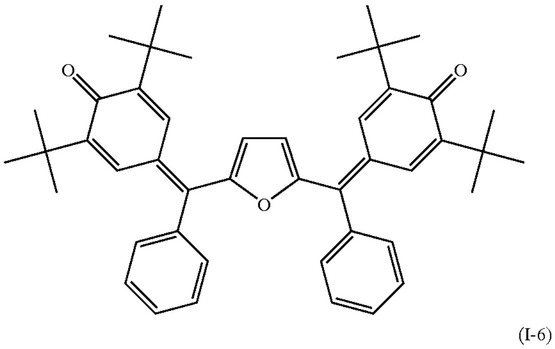
(I-6)
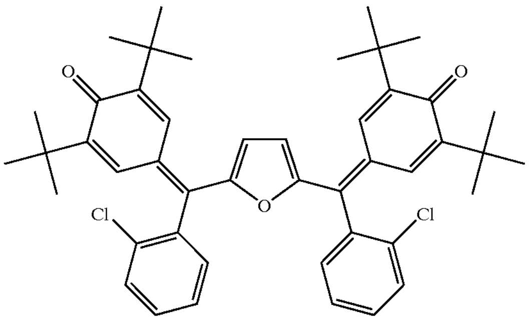
-continued
(I-7)
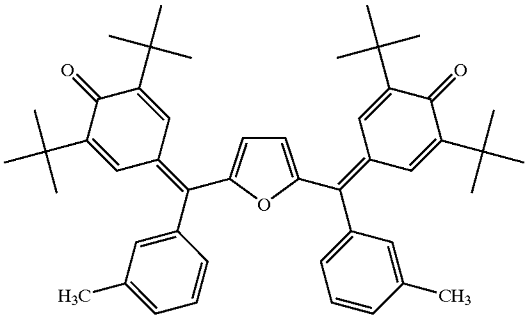
(I-8)
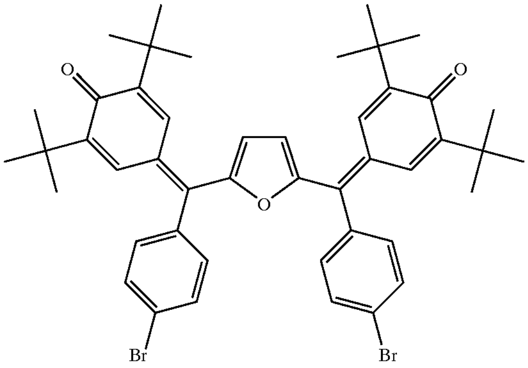
(I-9)
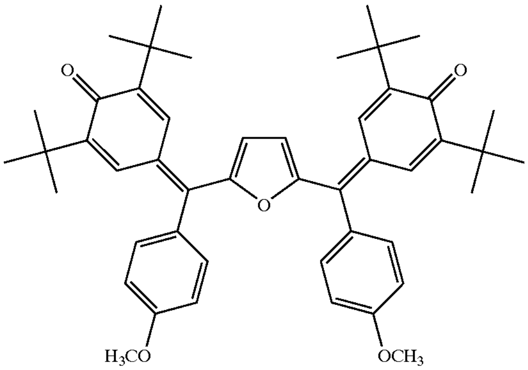
(I-10)
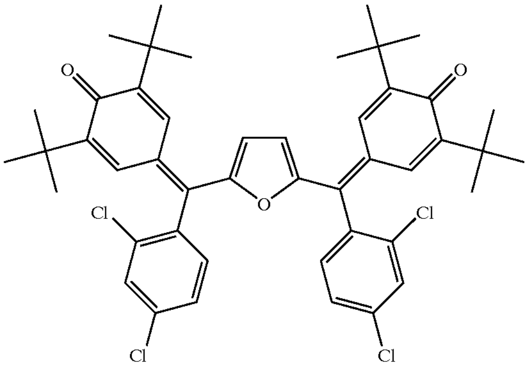

-continued
(I-11)
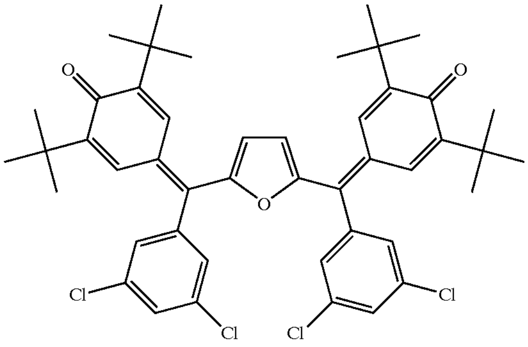
(I-12)
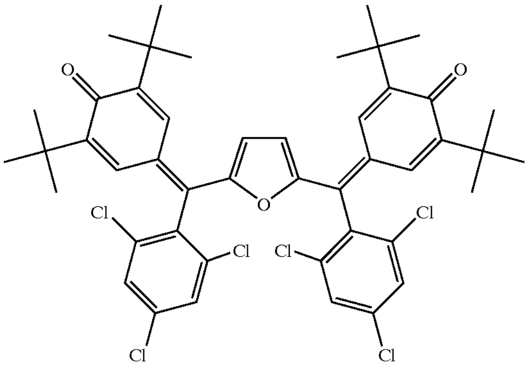
(I-13)
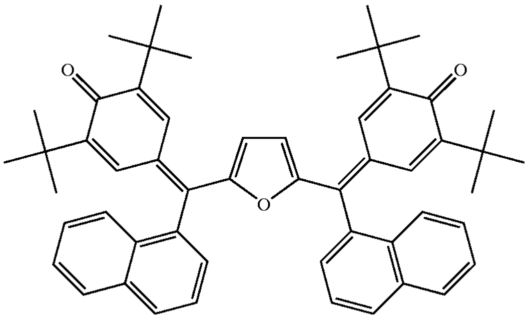
(I-14)
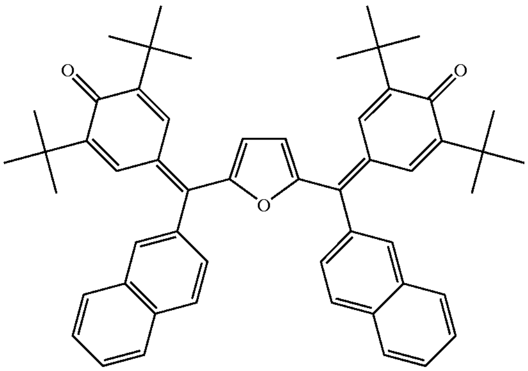
-continued
(I-15)
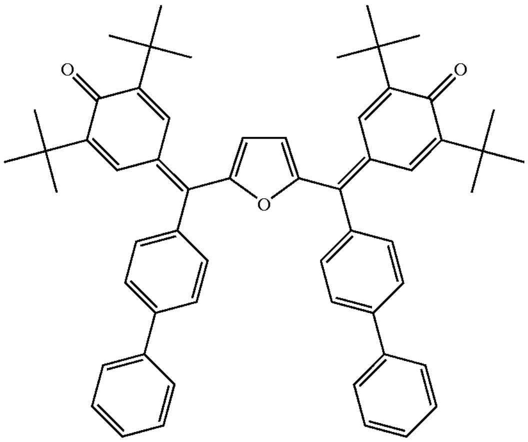
(I-16)
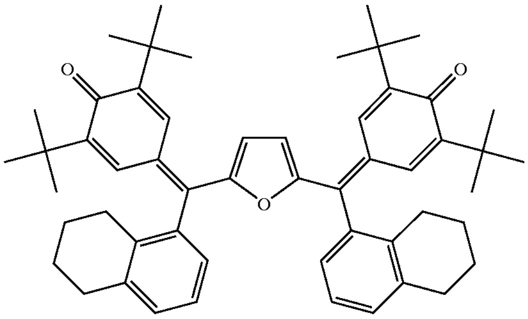
(I-17)
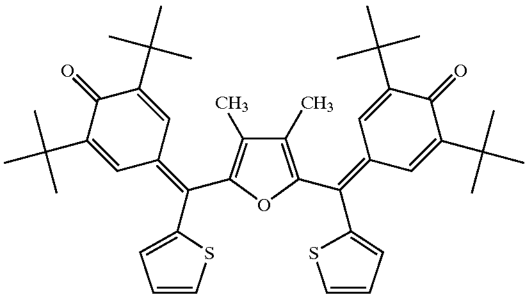
(I-18)
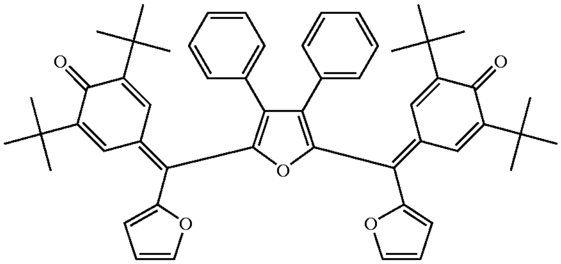

-continued
(I-19)
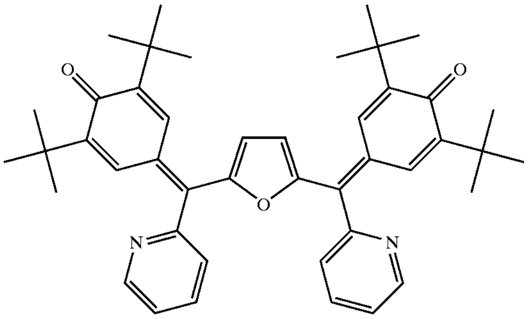
(I-20)
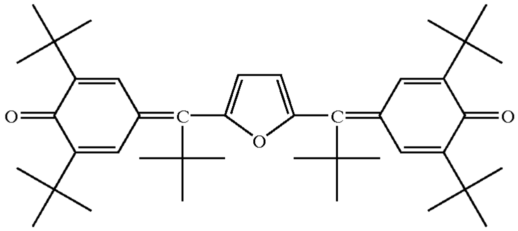
(I-21)
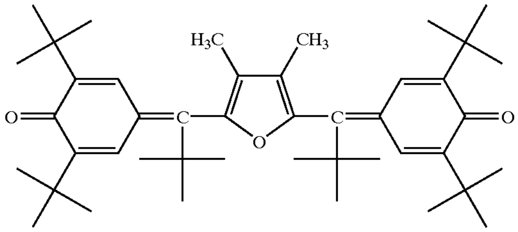
(I-22)
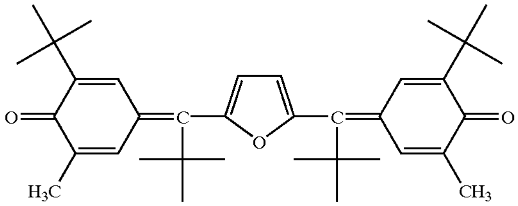
(I-23)
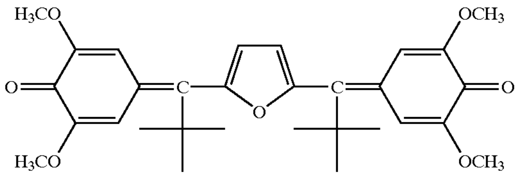
(I-24)
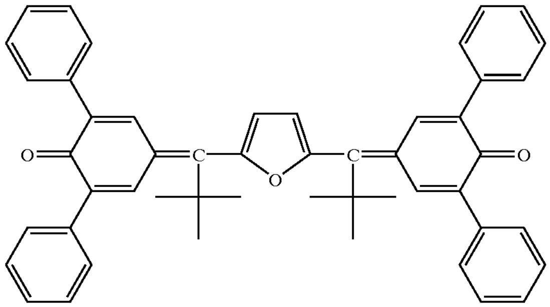
-continued
(I-25)
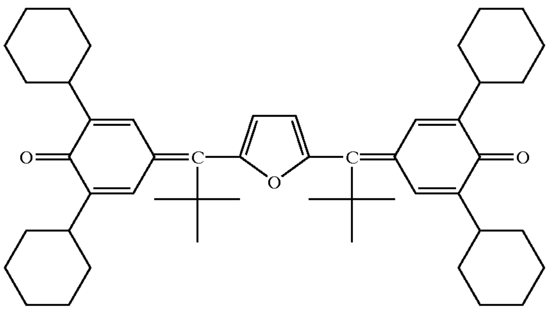
(I-26)
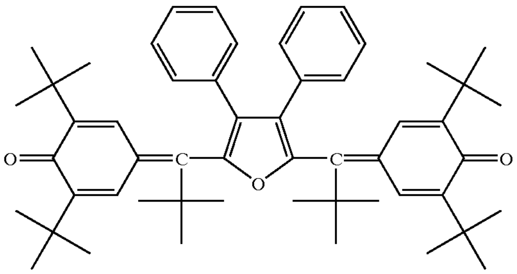
(I-27)
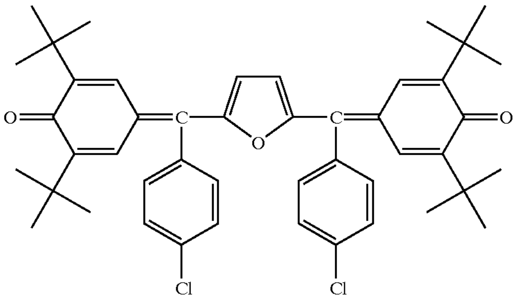
(I-28)
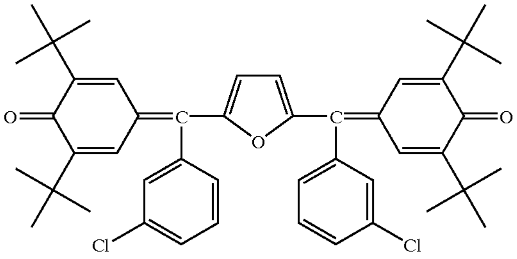
(I-29)
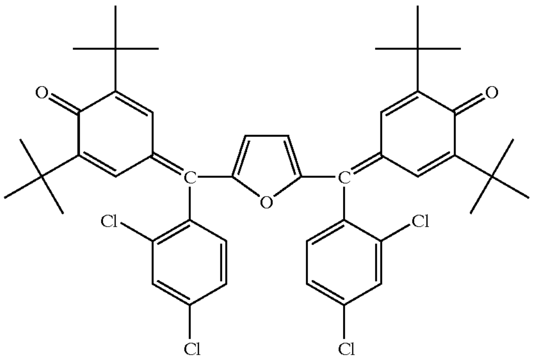

-continued
(I-30)
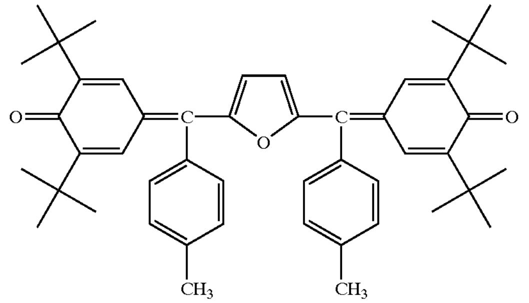
(I-31)
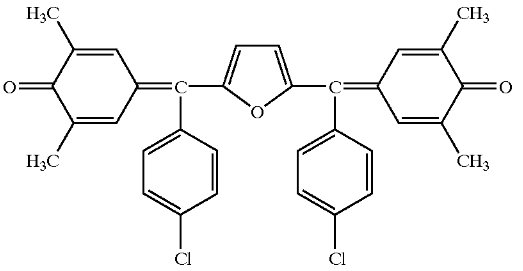
(I-32)
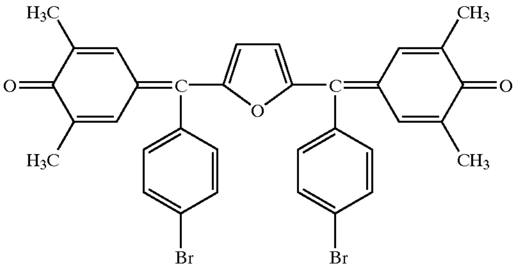
(I-33)
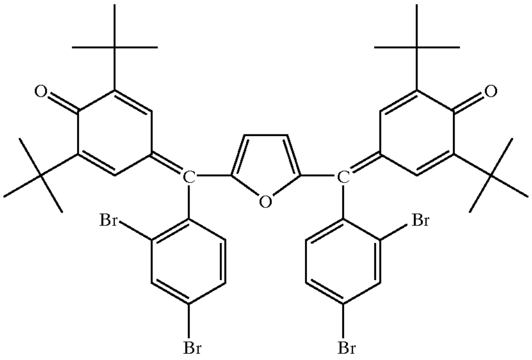
(I-34)
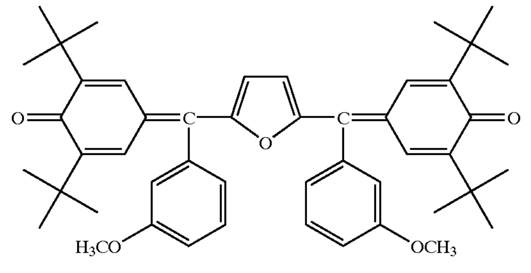
-continued
(I-35)
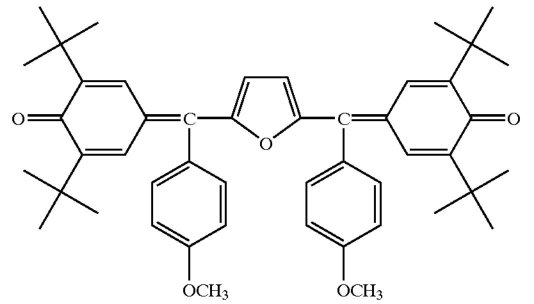
(I-36)
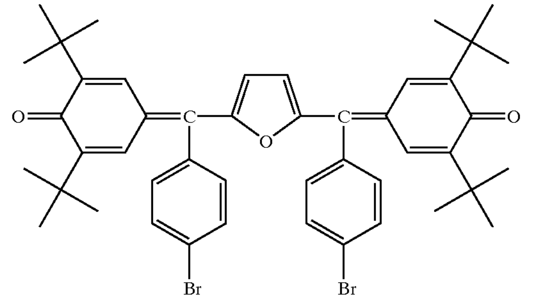
(I-37)
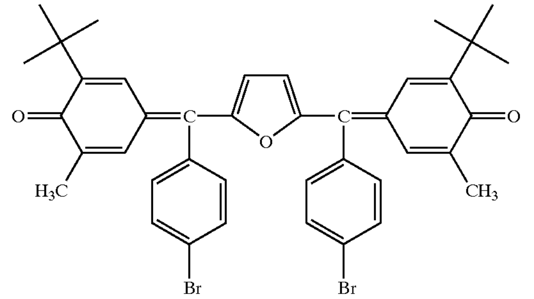
(I-38)
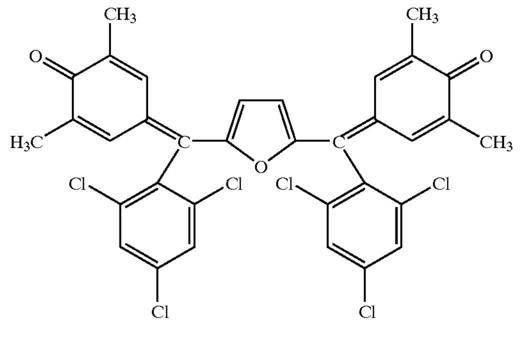

-continued
(I-39)
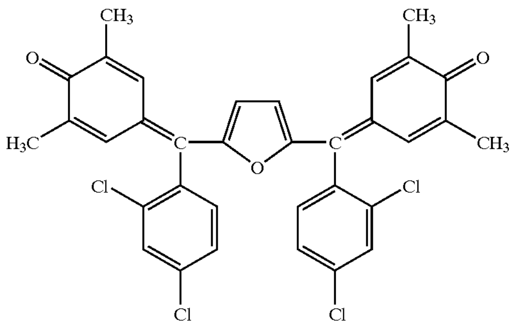
(I-40)
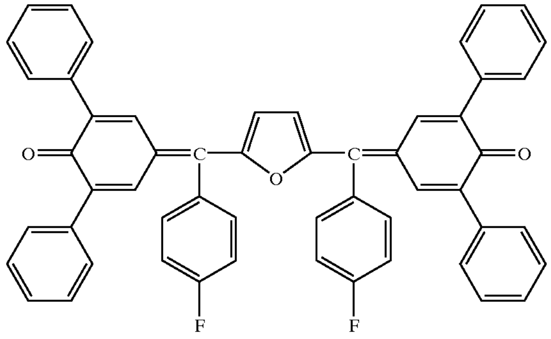
(I-41)
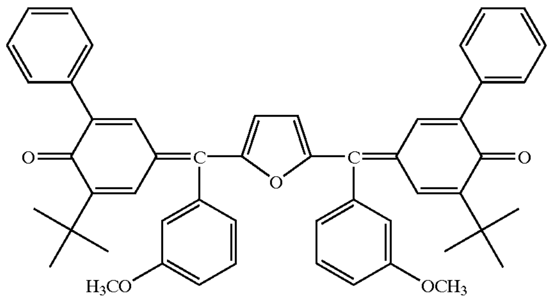
(I-42)
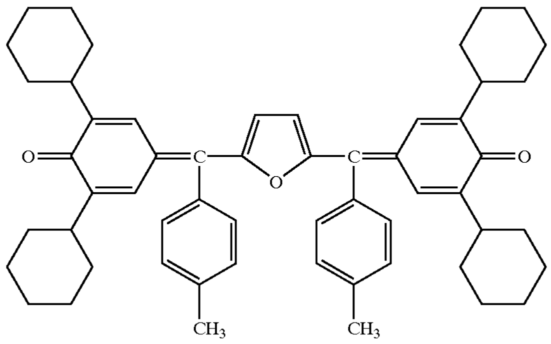
-continued
(I-43)
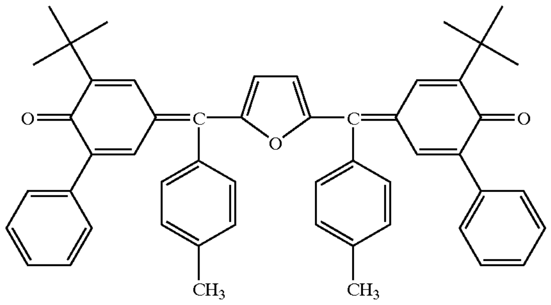
(I-44)
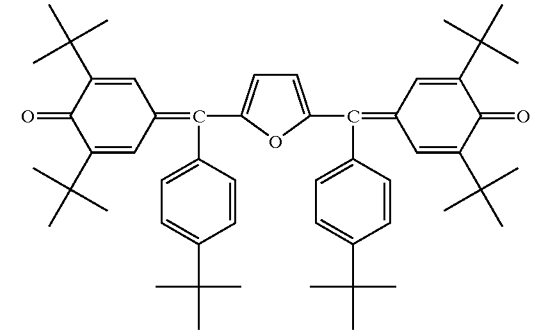
(I-45)
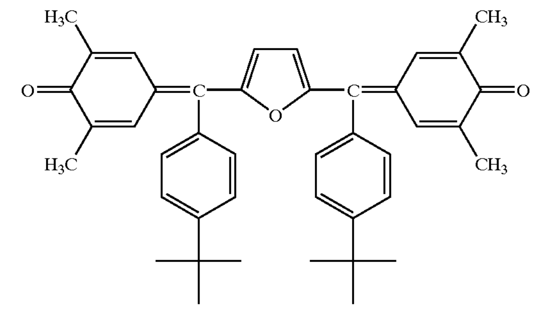
(I-46)
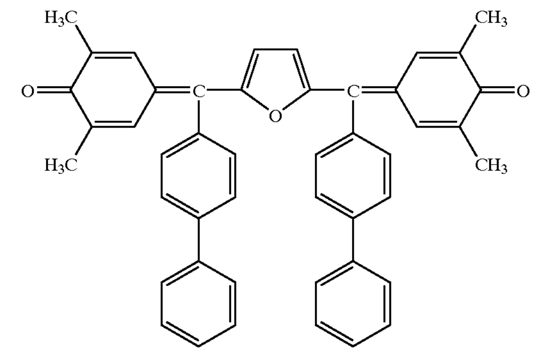

-continued
(I-47)
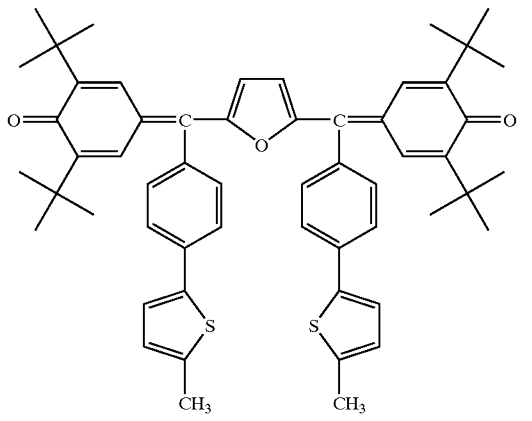
(I-48)
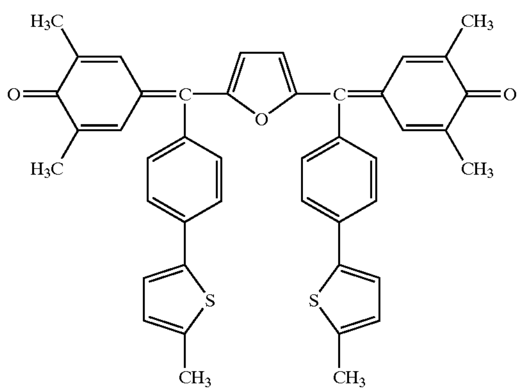
(I-49)
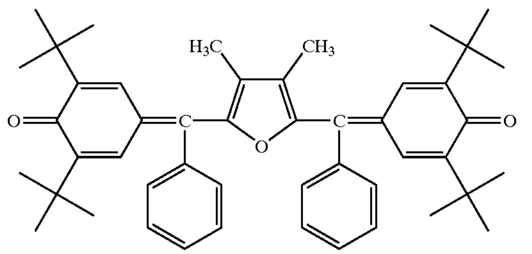
(I-50)
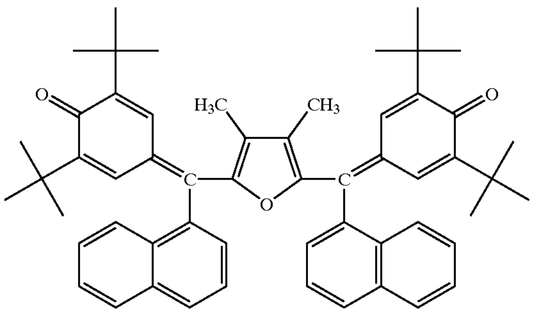
-continued
(I-51)
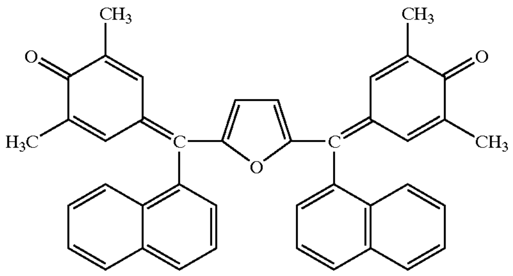
(I-52)
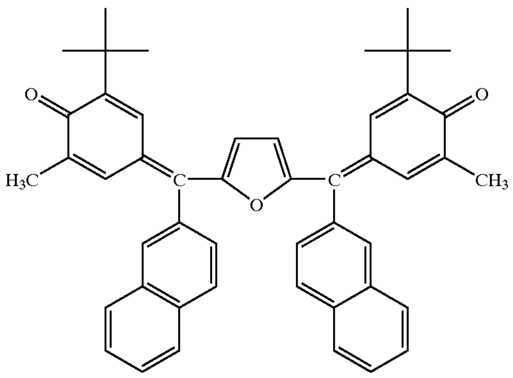
(I-53)
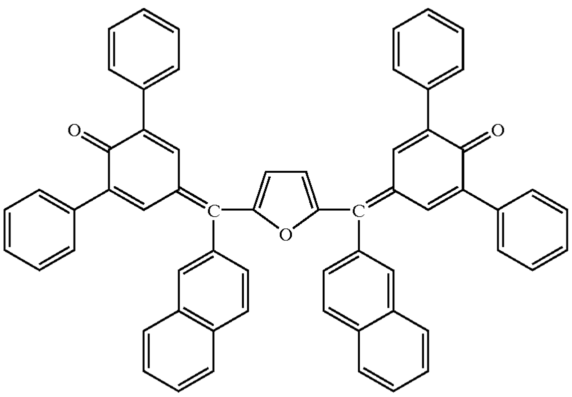
(I-54)
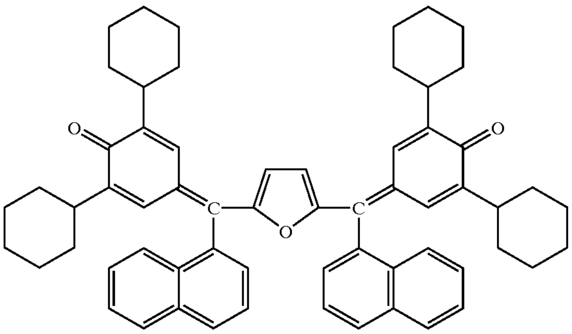

-continued (I-55)

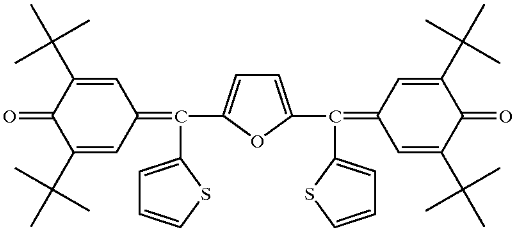

(I-56)

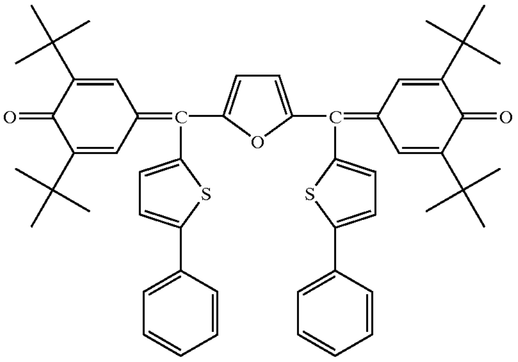

(I-57)

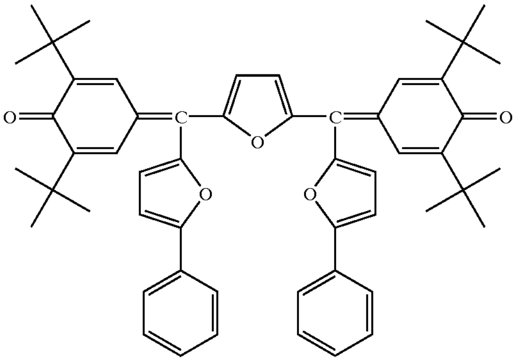

(I-58)

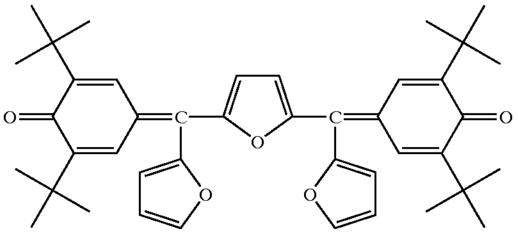

-continued (I-59)

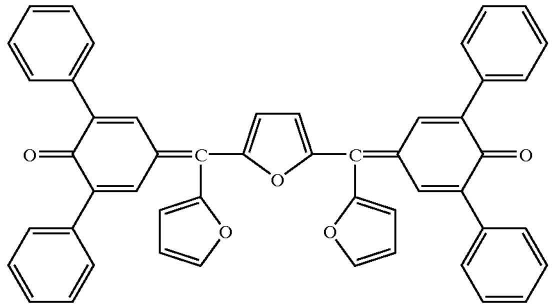

The quinomethane compounds according to embodiments of the present invention expressed by the above-described general formula (I) have an excellent electron transporting property. Thus, the compounds are useful as electron transporting materials and, in particular, may preferably be used as photosensitive materials for photoconductors for electrophotography and as functional layer materials, such as electron transporting layers for organic ELs.

The compounds according to embodiments of the invention may be synthesized according to, for example, the following reaction formula (1). Namely, as is shown in the following reaction formula (I), a compound expressed by the structural formula (1) may be synthesized by making a compound expressed by the following structural formula (A) and/or (A') and a compound expressed by the following structural formula (B) reacted using a suitable organometallic reagent (for example, n-butyllithium or the like), and thereafter removing a protecting group (TMS: trimethylsilyl group) to thus synthesize a compound expressed by the structural formula (C), which is further subjected to dehydrating condensation with a suitable catalyst (for example, p-toluenesulfonic acid or the like). Incidentally, TBAF in the following reaction formula (1) represents tetrabutyl ammonium fluoride.

Moreover, a compound expressed by the structural formula (B) may be synthesized by making a compound expressed by the following structural formula (E) and/or the following structural formula (E') and reacting with a furan compound expressed by the following structural formula (D). The compound expressed by the following structural formula (E) and/or the following structural formula (E') is obtained by taking a compound expressed by the following structural formula (F) and/or the following structural formula (F') as a starting material.

Reaction formula (I)

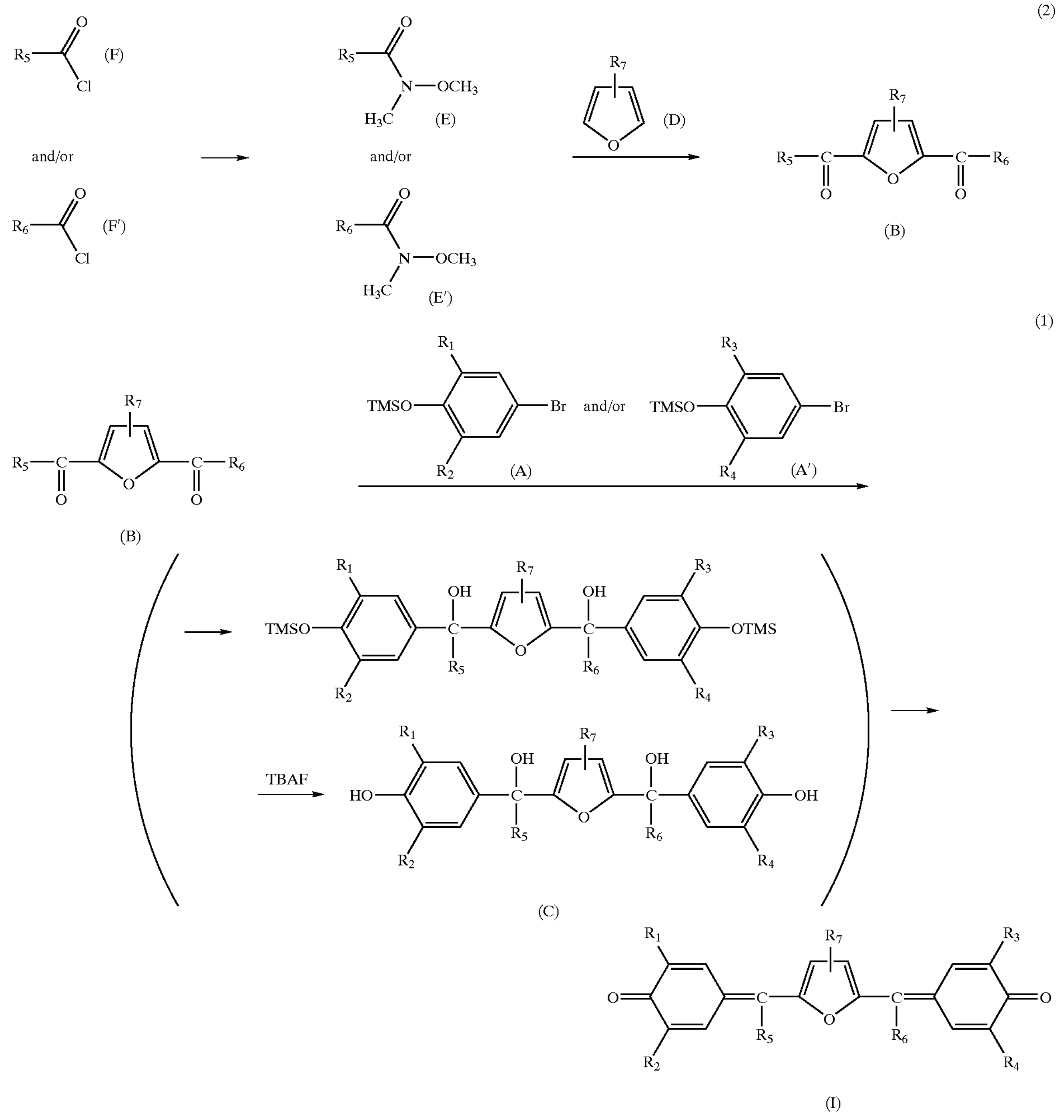

In the following, modes of the photoconductor for electrophotography for carrying out the invention will be explained in detail with reference to the drawings.

Figure 2:
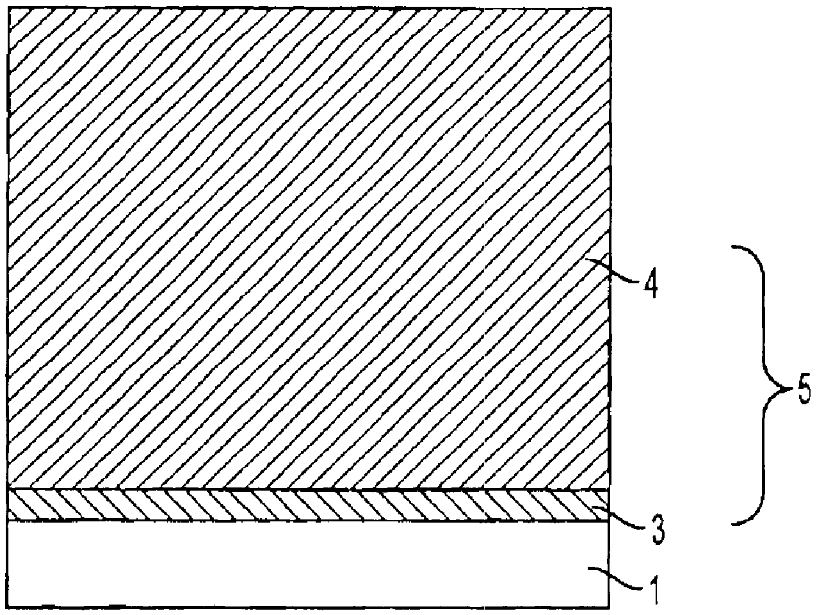
FIG. 2 is a schematic cross sectional view (not to scale) illustrating an example of a layered photoconductor for electrophotography in accordance with an embodiment of the present invention.

FIG. 1 and FIG. 2 are schematic cross sectional views showing examples of various kinds of arrangements of photoconductors. FIG. 1 shows an example of an arrangement of a single layered photoconductor. On a conductive substrate 1, an overcoat layer (a protective layer) 6 is layered on a single layer of a photosensitive layer 2 with a charge generating material and a charge transporting material dispersed in a resin binder (a binding agent) as required to make up the photoconductor. The single layered photoconductor may be manufactured by dispersing the charge generating material in a solution in which the charge transporting material and the resin binder are dissolved, and by applying the dispersion liquid on the conductive substrate. Further, when necessary, the overcoat layer 6 may be formed thereon.

FIG. 2 shows an example of an arrangement of a layered photoconductor. On the conductive substrate 1, a photosensitive layer 5 includes a charge generating layer 3 with a charge generating material as a principal material, and a charge transporting layer 4 containing a charge transporting material layered sequentially to make up the photoconductor. The layered photoconductor may be manufactured by forming the charge generating layer on the conductive substrate with the charge generating material deposited by vacuum evaporation or with a dispersion liquid that is applied and dried, which liquid is obtained by dispersing particles of the charge generating material in a solvent or a resin binder, and then forming the charge transporting layer thereon by applying with a solvent and drying, wherein the charge transporting material and the resin binder are dissolved in the solvent.

Moreover, although not shown, in any type of the photoconductors, an undercoat layer may be provided between the conductive substrate and the photosensitive layer. The undercoat layer may be provided as required to prevent injection of unnecessary charges from the conductive substrate into the photosensitive layer, to coat defects on the substrate, to improve adhesion of the photosensitive layer, and the like. The undercoat layer typically includes a layer with a resin taken as a principal component thereof, an oxide film such as anodized aluminum, or the like.

In the following, preferred modes of the photoconductor for electrophotography for carrying out the invention will be described for the layered photoconductor shown in FIG. 2. The invention, however, is not limited to the following specific examples.

The conductive substrate 1 plays a role as an electrode of the photoconductor and, at the same time, becomes a support for other layers with the shape thereof allowed to be any one of cylinder-like, plate-like and film-like. The conductive substrate may comprise, for example, a metal such as aluminum, stainless steel or nickel, or glass or resin with conduction treatment given thereon.

The charge generating layer 3 is formed by a process that applies a material with particles of charge generating material dispersed in a resin binder as described before or deposits the material by vacuum evaporation, and receives light to generate the charges. Moreover, it is important that the charge generating layer 3 has a high charge generating efficiency and, at the same time, a property of injecting generated charges to the charge transporting layer 4. In addition, it is desirable that the charge generating layer 3 has such a low electric field dependence that injection is performed effectively even under a low electric field.

For the charge generating materials, phthalocyanine compounds such as metal-free phthalocyanine and titanyl phthalocyanine, pigments or dyes of various compounds of azo, quinone, indigo, cyanine, squarillium, azulenium or pyrillium, or selenium or selenium compounds, from which a preferable material may be selected depending on a wavelength region of exposure light used for image forming, may be used. It is necessary only that the charge generating layer has a charge generating function. Therefore, the film thickness thereof is determined by the optical absorption coefficient of the charge generating materials, which is generally equal to or less than 5 $\mu$m, and preferably equal to or less than 2 $\mu$m. Furthermore, the charge generation layer may be used with a charge generating material that serves as the main component with a charge transporting material and the like added thereto.

For the resin binder for the charge generating layer 3, polymer and copolymer such as polycarbonate, polyester, polyamide, polyurethane, vinyl chloride, phenoxy resin, polyvinyl butyral, diallyl phthalate resin or methacrylate ester may be appropriately combined to be used.

The charge transporting layer 4 is a coated film with charge transporting materials being dispersed in a resin binder. In a dark place, the layer holds charges of the photoconductor as an insulator layer and, when receiving light, exhibits a function of transporting charges injected from the charge generating layer. As described above, in the present invention, it is necessary to prepare at least one kind of compound having an electron transporting property contained as such in a charge transporting material, for example, compounds that are expressed by the above-described general formula (I) according to the invention. However, another charge transporting material may be prepared. Preferred amounts of the compound to be added according to the present invention are preferably 10 to 60 weight percent to the total material contained in the charge transporting layer 4 and, more preferably, 15 to 50 weight percent.

For the resin binder for the charge transporting layer 4, polymer and copolymer and the like of polycarbonate, polyester, polystyrene or methacrylate ester may be used.

Moreover, to prevent deterioration by ozone when a photoconductor is used, an antioxidant agent such as an antioxidant of an amine series, a phenol series, a sulfur series, a phosphite series or a phosphorus series may be added in the charge transporting layer 4.

The protective layer 6 shown in FIG. 1 functions to receive and hold charges of corona discharge in a dark place, transmits light to which the photosensitive layer is sensitive, transmits light at an exposure that allows the light to reach the photosensitive layer, and receives injection of generated charges to neutralize and eliminate surface charges. Organic insulating film forming materials such as polyester and polyamide may be applied to the material of the protective layer. Moreover, the organic materials may be mixed with inorganic materials such as glass and $SiO_2$, and further, with materials lowering electric resistance such as metals and metallic oxides. It is desirable for the material for the overcoat layer to be as transparent as possible in a wavelength region in which the light absorption of the charge generating material is substantially at a maximum level.

The film thickness of the overcoat layer itself, although being dependent on the composition of the overcoat layer, may be determined arbitrarily within a range in which there is no adverse effect, such as an increase in residual potential when the photoconductor is continuously or repeatedly being used.

Also in the case of the single layered photoconductor shown in FIG. 1, it is necessary to make at least one kind of compound according to embodiments of the present invention that has an electron transporting property contained in the photosensitive layer 2, each compound being expressed by the above-described general formula (I). For the other materials, however, the same materials as those in the above-described layered photoconductor may be used without any particular limitation. As the charge transporting material, a hole transporting material is preferably prepared together with the compound expressed by the above-described general formula (I). As the hole transporting material, benzidine derivative, triphenylamine derivative and the like are preferable. In this embodiment, the preferred amounts of materials for addition to the total material contained in the applied film forming the photosensitive layer are preferably 10 to 60 weight percent of the total material, and, more preferably, are 15 to 50 weight percent of the total material. For the hole transporting materials, the amounts for addition are preferably 10 to 60 weight percent and, more preferably, 20 to 50 weight percent.

EXAMPLES

In the following, explanations will be made about examples according to embodiments of the invention.

Example 1 of the Photoconductor

Two parts by weight of titanyl phthalocyanine (TiOPc), 40 parts by weight of the compound expressed by the above-described structural formula (I-5), 60 parts by weight of triphenylamine derivative as a hole transporting material expressed by the following formula:

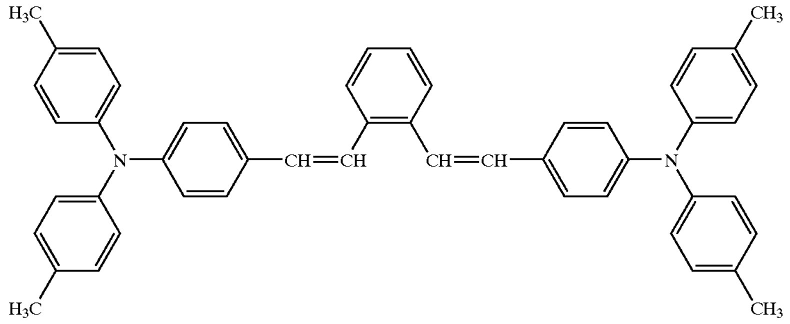

and 80 parts by weight of polycarbonate resin (BP-PC: Manufactured by Idemitsu Kosan Co., Ltd.) were kneaded together with methylene chloride by a mixing machine for 3 hours to prepare coating liquid. The coating liquid was applied to an aluminum support to form a photosensitive layer so that the film thickness thereof after drying was 20 μm, by which process a single layered photoconductor was manufactured.

Example 2 of the Photoconductor

In Example 2 of the photoconductor, a single layered photoconductor was manufactured in the same way as that in the Example 1, except that the compound expressed by the above-described structural formula (I-7) was used instead of the compound expressed by the above-described structural formula (I-5).

Example 3 of the Photoconductor

In Example 3 of the photoconductor, a single layered photoconductor was manufactured in the same way as that in the Example 1 except that the squarillium compound expressed by the following formula:

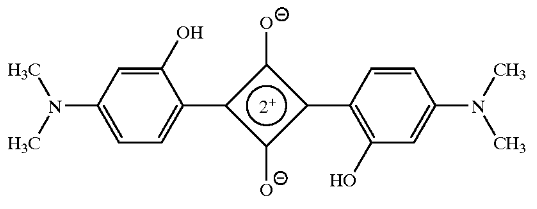

was used instead of titanyl phthalocyanine, and the compound expressed by the above-described structural formula (I-10) was used instead of the compound expressed by the above-described structural formula (I-5).

Example 4 of the Photoconductor

Two parts by weight of x-type metal-free phthalocyanine (H2Pc), 40 parts by weight of the compound expressed by the above-described structural formula (I-12), 60 parts by weight of benzidine derivative as a hole transporting material expressed by the following formula:

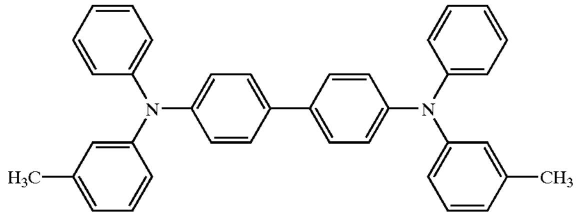

and 100 parts by weight of polycarbonate resin (PCZ200: Manufactured by Mitsubishi Gas Chemical Co., Ltd.) were kneaded together with methylene chloride by a mixing machine for 3 hours to prepare a coating liquid. The coating liquid was applied onto an aluminum support to form a photosensitive layer so that the film thickness thereof after drying was 25 μm, by which a single layered photoconductor was manufactured.

Example 5 of the Photoconductor

In Example 5 of the photoconductor, a single layered photoconductor was manufactured in the same way as that in Example 1, except that bisazo pigment expressed by the following formula:

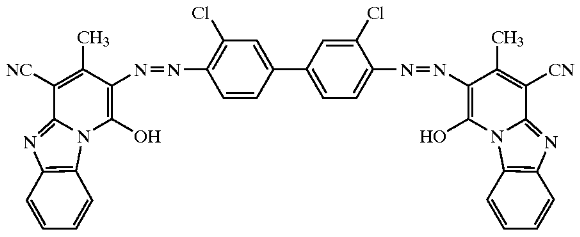

was used instead of titanyl phthalocyanine.

Example 6 of the Photoconductor

In Example 6 of the photoconductor, a single layered photoconductor was manufactured in the same way as that in the Example 1 except that bisazo pigment expressed by the following formula:

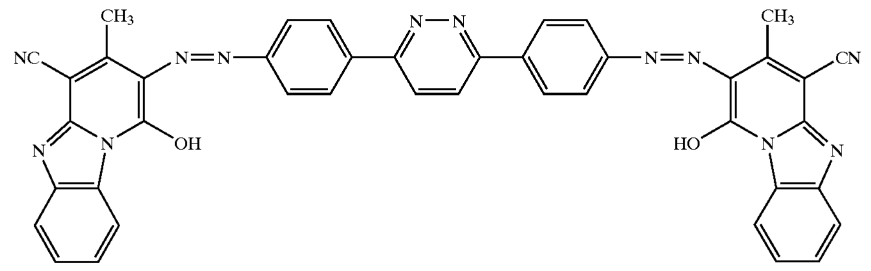

was used instead of titanyl phthalocyanine, and the compound expressed by the above-described structural formula (I-16) was used instead of the compound expressed by the above-described structural formula (I-5).

To determine the electrophotographic characteristics of the thus obtained photoconductor in each of the examples, measurements were carried out.

With an initial surface potential taken as Vs(V) when the surface of a photoconductor was made positively charged by carrying out corona discharge at +4.5 kV in a dark place, a surface potential Vd(V) was subsequently measured when the photoconductor was held for five seconds in a dark place with the corona discharge being stopped. Then, irradiation of white light was carried out with an illuminance of 100 lax, and a time (sec) until Vd was reduced to a half of an original value was obtained as a sensitivity $E_{1/2}$(lux·s). Moreover, for each of the Examples 1 to 4, a time (sec) was obtained for the time required for Vd to be reduced to a half of an original value when irradiation with monochromatic light (780 nm) of 1 $\mu$W was carried out, from which time a sensitivity $E_1/_2(\mu J/cm^2)$ was obtained. Further, for each Example, a residual potential Vr(V) was measured when irradiation with the white light or the monochromatic light was carried out for ten seconds on the surface of the photoconductor. Results of the measurements are shown in the following Table 1.

TABLE 1

| | White light | | 780 nm Monochromatic light | |
|---|---|---|---|---|
| | Sensitivity (lux · s) | Residual potential (V) | Sensitivity ($\mu J/cm^2$) | Residual potential (V) |
| Example 1 | 1.0 | 70 | 0.8 | 60 |
| Example 2 | 1.3 | 90 | 1.1 | 80 |
| Example 3 | 0.8 | 50 | 0.5 | 40 |
| Example 4 | 1.2 | 60 | 0.7 | 60 |
| Example 5 | 1.2 | 80 | — | — |
| Example 6 | 1.6 | 90 | — | — |

Example 1 of Synthesis

Synthesis of the Compound of the Above-Described Specific Example (I-5)

Reaction formula (1-1)

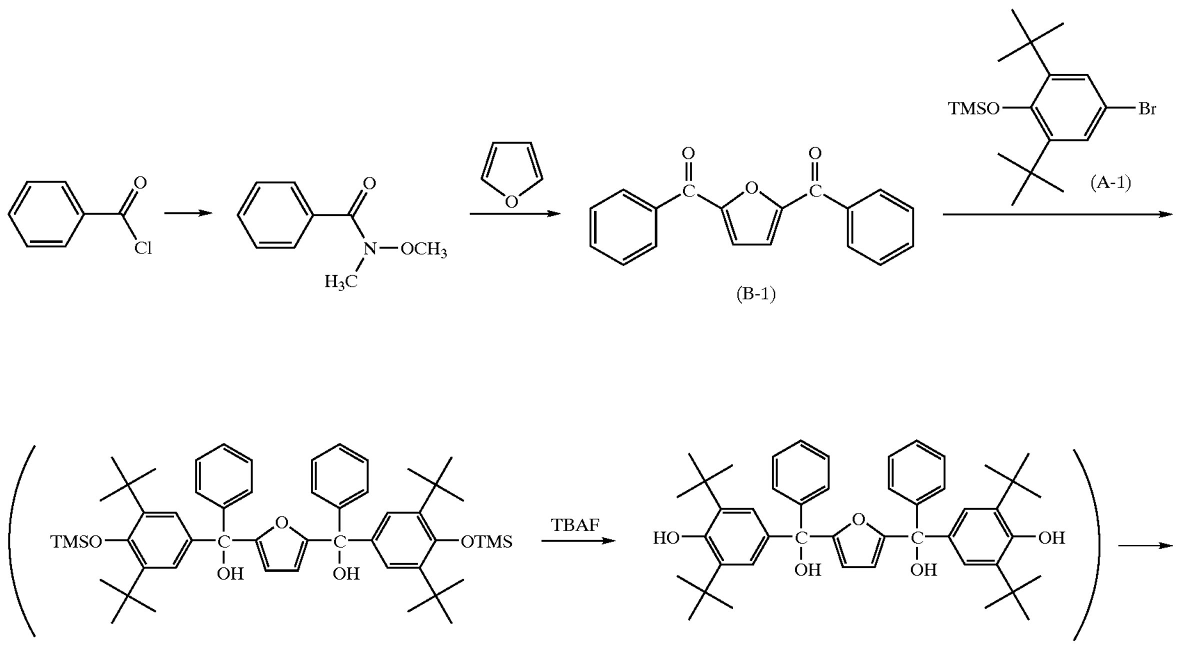

-continued

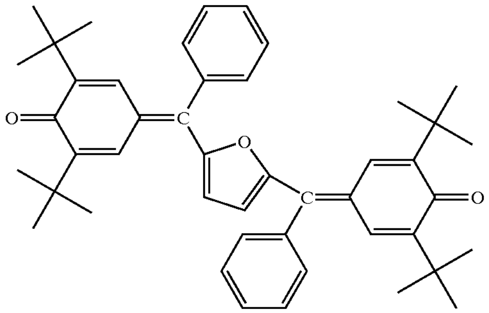

(I-5)

| Step (1) Raw material, Reagent | |
|---|---|
| Benzoyl chloride | 200 mmol (28.1 g) |
| N,O-dimethylhydroxylamine hydrochloride | 220 mmol (21.5 g) |
| Dichloromethane | 200 ml |
| Pyridine | 460 mmol (36.4 g) |

Operation (1) In a three-necked flask, 4-chlorobenzoyl chloride and N,O-dimethylhydroxylamine were put, to which dichloromethane (200 ml) was added.

(2) At 0° C. (ice bath) under an atmosphere of nitrogen, pyridine was dropped in thirty minutes, and was thereafter stirred at room temperature for two hours.

(3) About 100 ml of water was added to finish the reaction and an organic layer was extracted. Further, the water layer was extracted by 100 ml of dichloromethane, cleaned together with the above organic layer by 1 N of HCl water solution and thereafter condensed.

(4) Oily matter was separated and purified by column chromatography (silica gel, mobile phase: dichloromethane).

As a result of this, N-methoxy-N-methylbenzamide was obtained. The yield was 33.3 g (83.4% of yield), MS m/z165 (M+).

| Step (2) Raw material, Reagent | |
|---|---|
| Furan | 30 mmol (2.04 g) |
| Tetramethylethylenediamine | 66 mmol (7.67 g) |
| Hexane | 20 ml |
| n-Butyllithium (1.6 M hexane solution) | 66 mmol (41 ml) |
| THF (tetrahydrofuran) | 75 ml |
| N-methoxy-N-methylbenzamide | 75 mmol (12.4 g) |
| THF (tetrahydrofuran) | 20 ml |

Operation (1) In a three-necked flask, furan and tetramethylethylenediamine were put, to which hexane was added.

(2) At 0° C. (ice bath) under an atmosphere of nitrogen, n-butyllithium was dropped in fifteen minutes, was stirred for thirty minutes, and was thereafter stirred at room temperature for thirty minutes before being heated and circulated for thirty minutes.

(3) After cooling the above-described reacted liquid down to room temperature, THF (75 ml) was added.

(4) At −40° C. to −30° C. (dry-ice-ethanol bath) under an atmosphere of nitrogen, a THF solution of N-methoxy-N-methylbenzamide was dropped in fifteen minutes, and was stirred for one hour.

(5) The reacted liquid was slowly brought back to room temperature and stirred for thirty minutes.

(6) The reacted liquid was poured into ice water to be stirred.

(7) A precipitate was filtered and cleaned with ethanol.

As a result of these Steps (1) and (2), 2,5-dibenzoylfuran expressed by the above-described formula (B-1) was obtained. The yield was 2.3 g (27.7% of yield), MS m/z276 (M+).

| Step (3) Raw material, Reagent | |
|---|---|
| 4-bromo-2,6-di-t-butyl-1-[trimethylsilyl]benzene (A-1) | 45 mmol (16.1 g) |
| THF (tetrahydrofuran) | 90 ml |
| n-Butyllithium (1.6 M hexane solution) | 54 mmol (34 ml) |
| 2,5-Dibenzoylfuran (B-1) | 15 mmol (4.1 g) |
| THF (tetrahydrofuran) | 30 ml |
| Ammonium chloride water solution | 10 ml |
| Tetrabutyl ammonium fluoride (1.0 M THF solution) (TBAF) | 45 mmol (45 ml) |
| p-Toluenesulfonic acid monohydrate (p-TsOH) | approximately 50 mg |
| Toluene | 100 ml |

Operation (1) The above-described compound (A-1) was weighed to be put in a three-necked flask with THF (90 ml) added thereto.

(2) At −78° C. (dry-ice-ethanol bath) under an atmosphere of nitrogen, n-butyllithium was dropped in thirty minutes, and was stirred for thirty minutes. Thereafter, a THF solution (30 ml) of the above-described compound (B-1) was dropped therein in thirty minutes to be stirred for three hours under the same condition.

(3) About 10 ml of a water solution of saturated ammonium chloride was added for hydrolysis.

(4) At 0° C. (ice bath), TBAF (45 ml) was added to be stirred for three minutes.

(5) The obtained reacted solution was poured into ice water to be stirred.

(6) Extraction with dichloromethane was carried out, and the extracted material was made condensed.

(7) Solid matter was dissolved in toluene (100 ml). Approximately 50 mg of p-TsOH was added to the solution, which was then heated and circulated for two hours.

(8) After the reaction was completed, the solution was condensed.

(9) Solid matter was filtered, cleaned with a small amount of hexane, and thereafter recrystallized by hexane.

Figure 3:
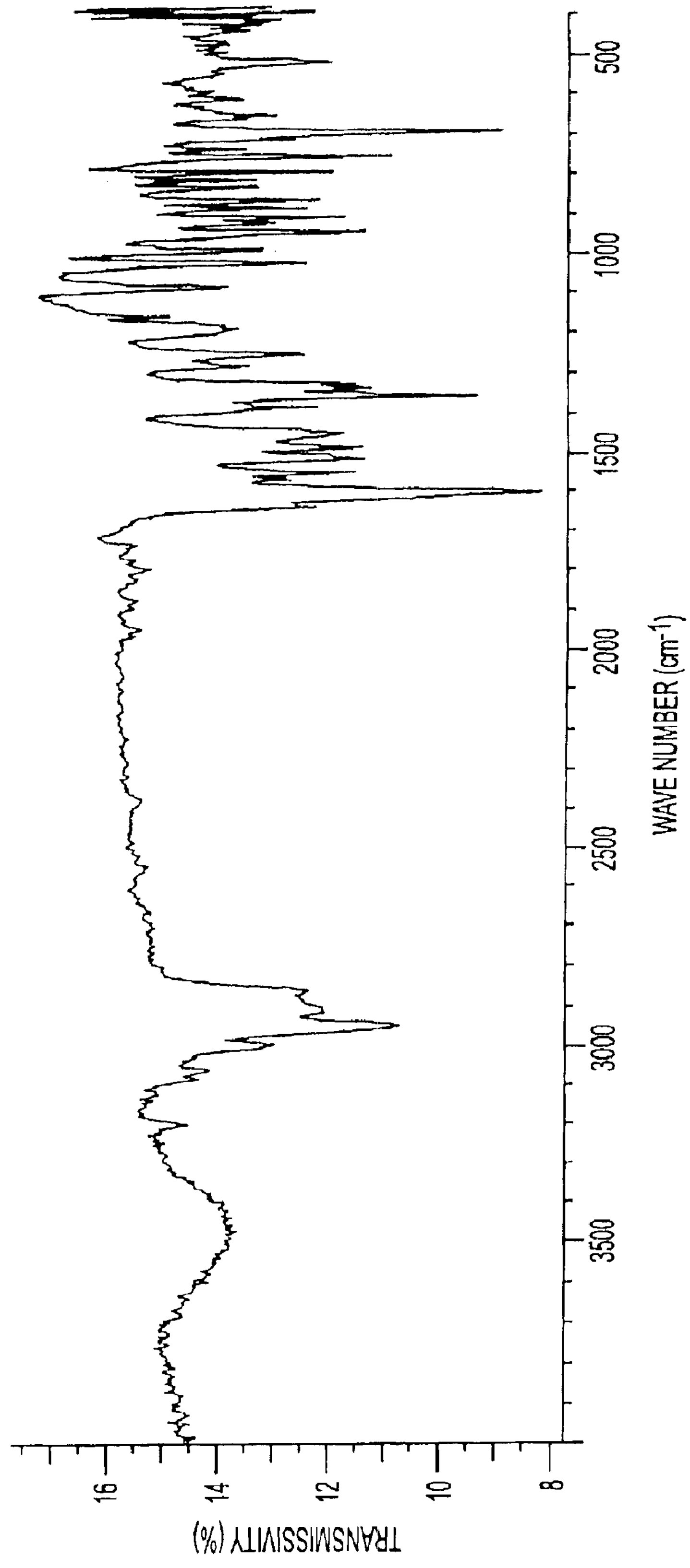
FIG. 3 is an IR spectrum of a compound expressed by the structural formula (I-5)
Figure 4A:
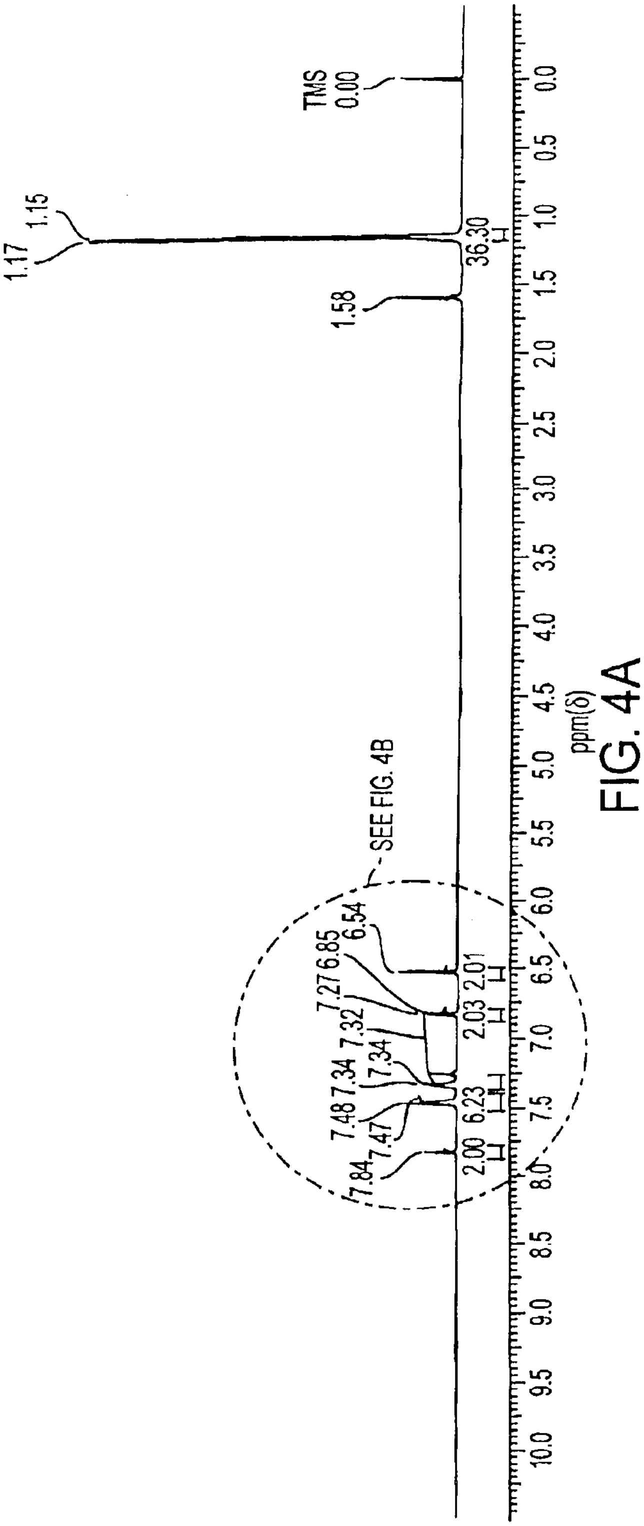
FIGS. 4A–4B are an $^1$H-NMR spectrum of the compound expressed by the structural formula (I-5) and an enlarged portion thereof, respectively.
Figure 4B:
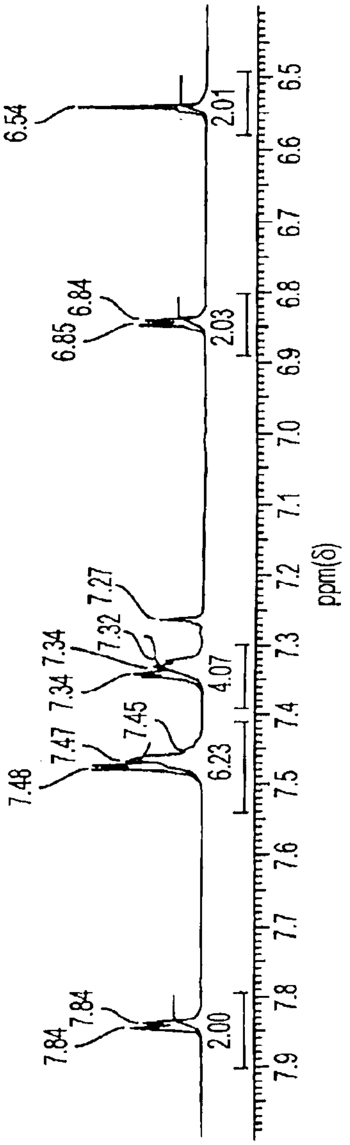

As a result of this Step (3), a compound expressed by the above-described formula (I-5) was obtained. The yield was 6.6 g (67.4% of yield), MS m/z652 (M+). An IR spectrum of the compound of the specific example (I-5) is shown in FIG. 3, and an $^1$H-NMR spectrum and an enlarged portion thereof are shown in FIG. 4A and FIG. 4B, respectively.

Example 2 of Synthesis

Synthesis of the Compound of the Above-Described Formula (I-27)

Figure 5:
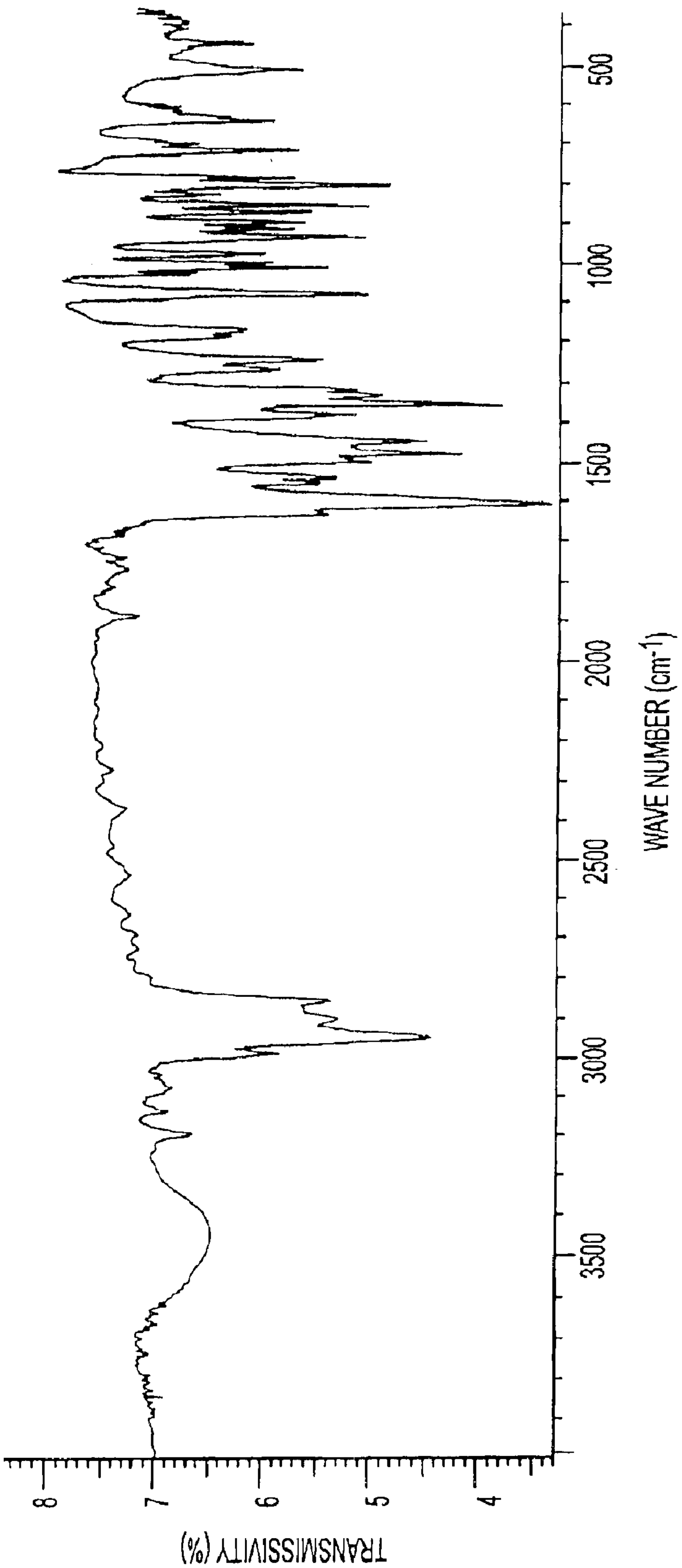
FIG. 5 is an IR spectrum of a compound expressed by the structural formula (I-27)
Figure 6A:
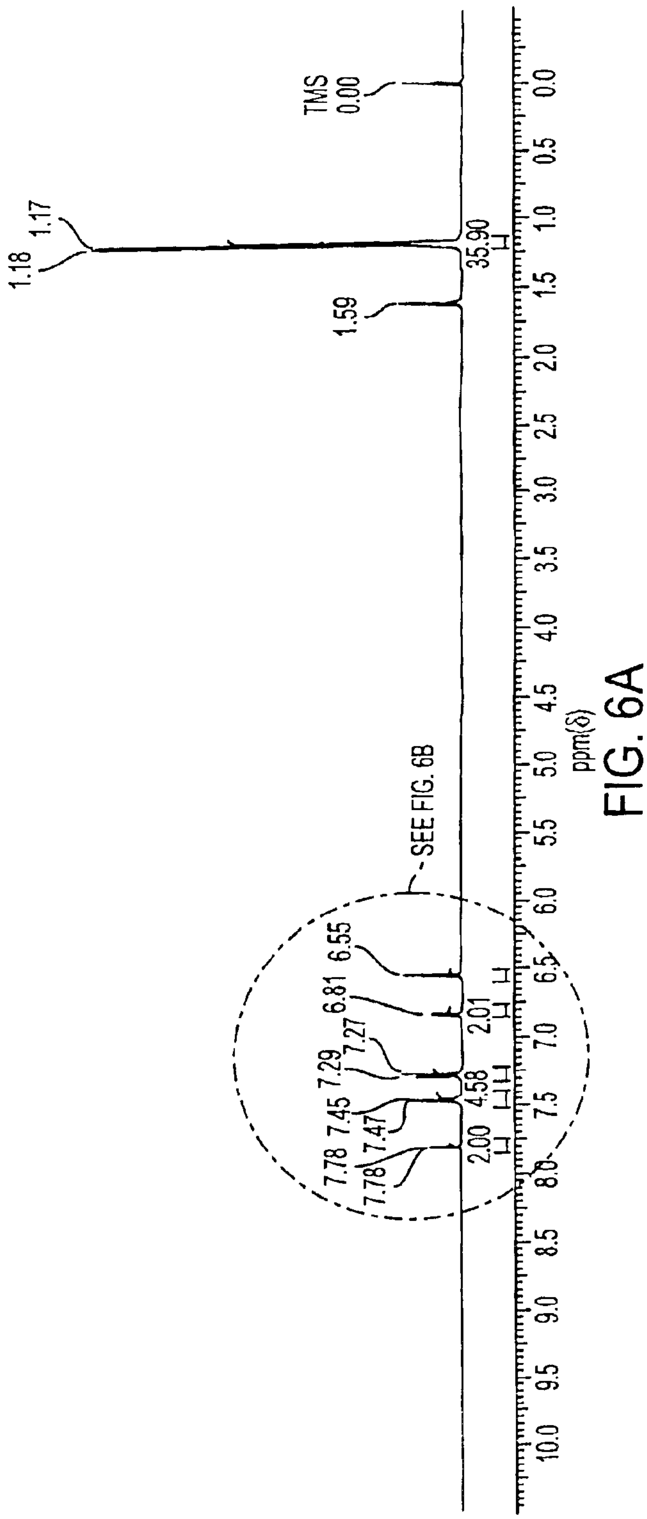
FIGS. 6A–6B are an $^1$H-NMR spectrum of the compound expressed by the structural formula (I-27) and an enlarged portion thereof, respectively.
Figure 6B:
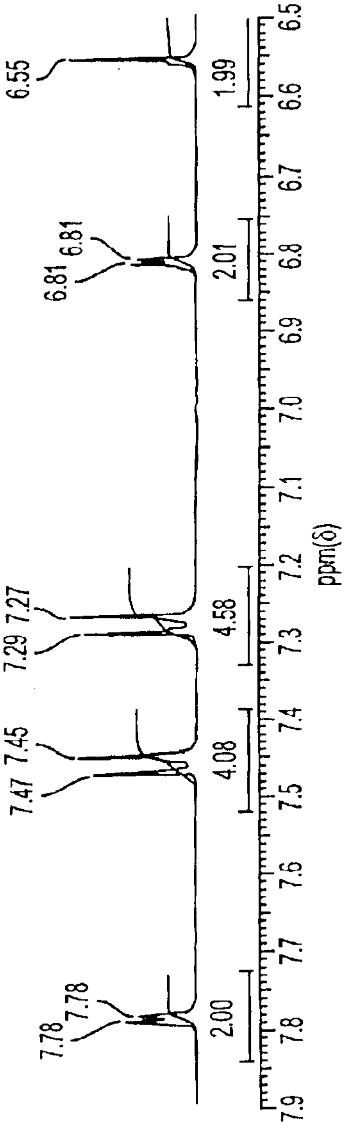

Except that benzoyl chloride in the above-described Example 1 of synthesis was substituted by 4-chlorobenzoyl chloride, the same operation was carried out to obtain a compound expressed by the above-expressed formula (I-27). The yield was 5.4 g (50.1% of yield), MS m/z720 (M+). An IR spectrum of the compound of the specific example (I-27) is shown in FIG. 5, and an $^1$H-NMR spectrum and an enlarged portion thereof are shown in FIG. 6A and FIG. 6B, respectively.

Moreover, 4-bromo-2,6-di-tert-butyl-1-[trimethylsilyl] benzene (the above-described formula (A-1)) may be synthesized by a known method described in, for example, JP-A-2001-222122 and the like.

Reaction formula (I-2)

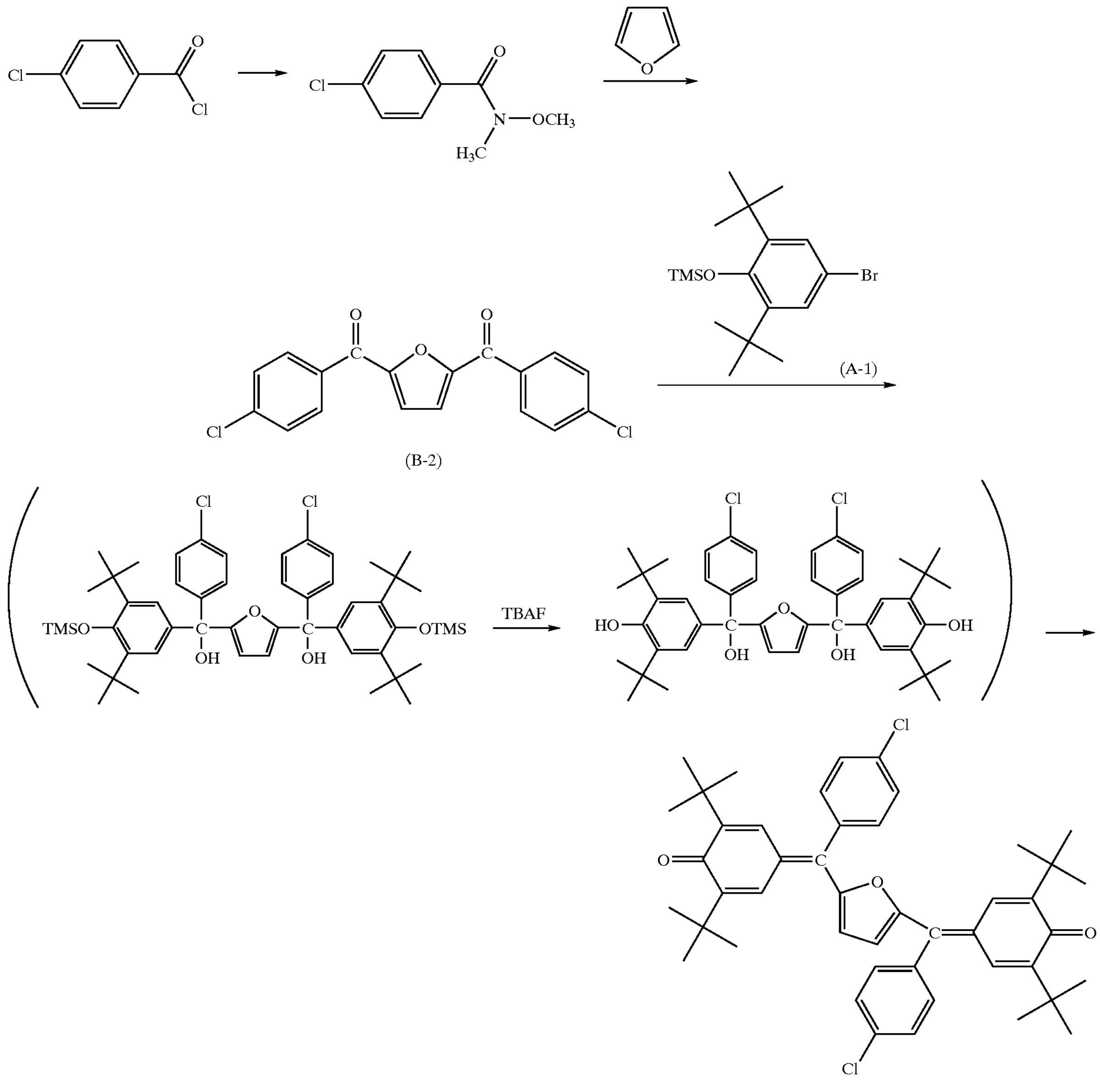

(A-1)

(B-2)

(I-27)

Example 7 of the Photoconductor

A plate-like photoconductor for evaluation of electrical characteristics and a drum-like photoconductor (having a diameter of 30 mm) for evaluation of printing were manufactured.

On each of an aluminum plate and an aluminum pipe material, an undercoat layer solution with the following composition was dip coated and then dried at 100° C. for sixty minutes to be formed in an undercoat layer with a film thickness of 0.3 μm. In the following, the term "parts" represents parts by weight.

| | |
|---|---|
| Soluble nylon (Amyran CM8000: Manufactured by Toray Industries, Inc.) | 3 parts |
| Methanol/methylene chloride mixed solvent (5/5) | 97 parts |

Next, a dispersion liquid for a single layered photosensitive layer with the following composition was dip coated and then dried at 100° C. for sixty minutes to be formed into a single layered photosensitive layer with a film thickness of 25 μm.

| | |
|---|---|
| Charge generating material: X-type metal-free phthalocyanine | 0.3 parts |
| Hole transporting material: triphenylamine derivative expressed by the following structural formula (HT1): | 7 parts |

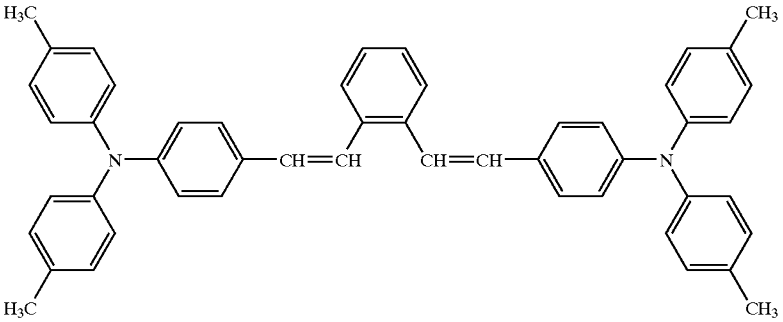

(HT1)

| | |
|---|---|
| Electron transporting material: Compound expressed by the above-described formula (I-8) | 3 parts |
| Antioxidant agent: 3,5-di-tert-4-hydroxytoluene (BHT) (Manufactured by Tokyo Chemical Industry Co., Ltd.) | 1 part |
| Silicone oil: KF-50 (Manufactured by Shin-Etsu Chemical Co., Ltd.) | 0.01 parts |
| Binder resin: Bisphenol Z-type polycarbonate resin (PANLITE TS2020: Manufactured by Teijin Chemical Co., Ltd.) | 10 parts |
| Methylene chloride | 100 parts |

As described above, photoconductors for electrophotography were manufactured.

Example 8 of the Photoconductor

Except that 3 parts of the electron transporting material expressed by the above-described formula (I-5) was substituted by 3 parts of the electron transporting material expressed by the above-described formula (I-27) synthesized in the Example 2 of synthesis in the composition of the dispersion liquid for a photosensitive layer used in the Example 1 of the photoconductor, a photoconductor was manufactured in the same way as that in the Example 1 of the photoconductor.

Evaluations of the Examples 7 and 8 of the Photoconductors

For evaluating electrical characteristics, by using the plate-like photoconductors, evaluations were carried out by the electrostatic copying paper testing apparatus EPA-8100 manufactured by Kawaguchi Denki Seisakusho Co., Ltd.

Under an environment at 23° C. in temperature, 45% in humidity and in the dark place, each of the photoconductors was made charged so that the surface potential became about +600 V and a retention rate of the surface potential in the subsequent five seconds until exposure was obtained by the following expression:

$$\text{Retention rate } V_{k5}(\%)=(V5/V0)\times100,$$

where

V0: the surface potential immediately after the exposure; and

V5: the surface potential after five seconds (at the start of the exposure).

Then, with the surface potential at +600 V in the same way, exposure under 1.0 μW/cm$^2$ monochromatic light, isolated to have a wavelength of 780 nm from the light of a halogen lamp by a filter, was carried out for five seconds. An amount of exposure required for reducing the surface potential to a half of the original surface potential (+300 V) was obtained as a sensitivity $E_{1/2}$(μJ/cm$^2$), and the surface potential five seconds after the exposure was obtained as a residual potential Vr (V). The results of the evaluations are shown in Table 2.

TABLE 2

| | Retention rate $V_{k5}$ (%) | Sensitivity $E_{1/2}$ (μJ/cm$^2$) | Residual Potential $V_r$ (V) |
|---|---|---|---|
| Example 7 of Photoconductor | 85.2 | 0.48 | 66 |

TABLE 2-continued

| | Retention rate $V_{k5}$ (%) | Sensitivity $E_{1/2}$ ($\mu J/cm^2$) | Residual Potential $V_r$ (V) |
|---|---|---|---|
| Example 8 of Photoconductor | 82.5 | 0.42 | 57 |

As an evaluation of durability by actual printing, with a drum-like photoconductor mounted on a laser printer HL-1240 manufactured by Brother Industries, Ltd., a solid black image, a solid white image and a halftone image were printed under an environment at a temperature of 25° C. and a humidity of 52%. Subsequent to this, images each with printing rate of about 5% were printed on five thousand sheets. Thereafter, a solid black image, a solid white image and a halftone image were printed again to evaluate images after printing five thousand sheets.

As a result, in the evaluations of the Examples 7 and 8 of the photoconductors, excellent images were obtained in both of the initial images and the images after printing five thousand sheets.

As described above, according to embodiments of the present invention, in a photosensitive layer provided on a conductive substrate, a compound having an electron transporting property expressed by the above-described general formula (I) was used as a charge transporting material to obtain a photoconductor with a high sensitivity and excellent electrical characteristics when being positively charged. Moreover, for the charge generating material, a suitable material may be selected in accordance with a kind of exposure light utilized. Thus, by using phthalocyanine compound, squarillium compound, bisazo compound and the like, a photoconductor may be obtained for a semiconductor laser printer and copying machine. Furthermore, an overcoat layer is provided on the surface to improve durability.

In addition, according to embodiments of the invention, compounds having an excellent electron transporting property may be used. By using the compounds for electronic devices using organic compounds such as photoconductors for electrophotography and organic ELs, characteristics thereof such as electrical characteristics and light emitting efficiencies may be improved.

Figure 7:
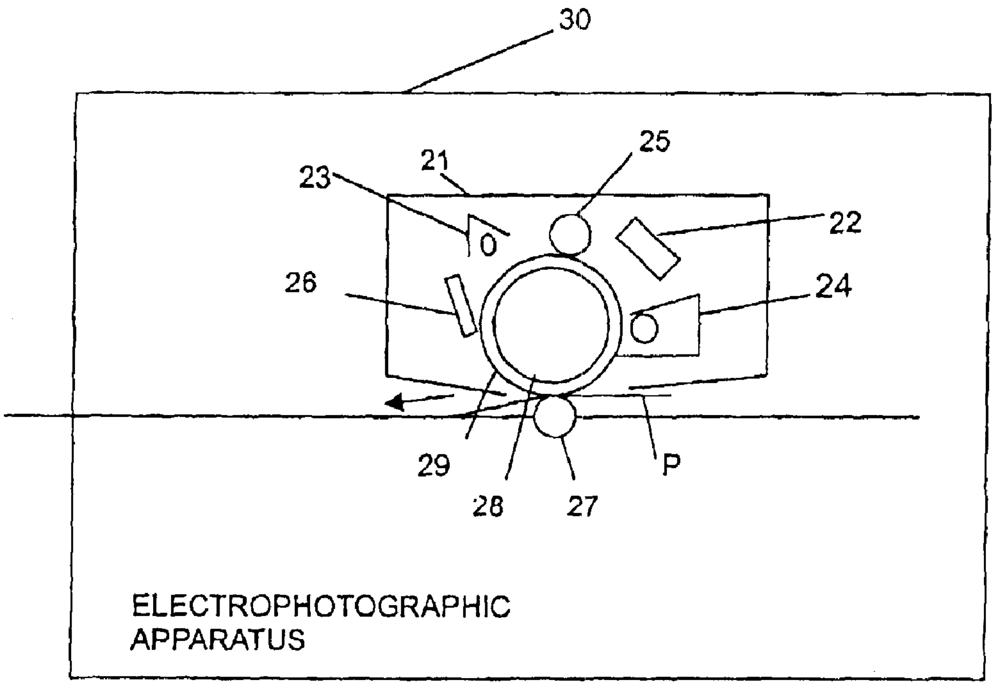
FIG. 7 is a block diagram of an electrophotographic apparatus having an electrophotographic cartridge and an electrophotographic photoconductor drum in accordance with an embodiment of the present invention.

As shown in FIG. 7, embodiments of the present invention may be utilized in an electrophotographic cartridge 21, an electrophotographic photoconductor drum 28, or in an electrophotographic apparatus 30. The electrophotographic cartridge 21 typically comprises an electrophotographic photoconductor 29 and at least one of a charging device 25 that charges the electrophotographic photoconductor 29, a developing device 24 which develops an electrostatic latent image formed on the electrophotographic photoconductor 29, and a cleaning device 26 which cleans a surface of the electrophotographic photoconductor 29. The electrophotographic cartridge 21 is attachable to/detachable from the electrophotographic apparatus 30, and the electrophotographic photoconductor 29 is described more fully above.

The electrophotographic photoconductor drum 28,29 for an electrophotogarphic apparatus 30, generally includes a drum 28 that is attachable to and detachable from the electrophotographic apparatus and that includes an electrophotographic photoconductor 29 installed thereon, wherein the electrophotographic photoconductor 29 is described more fully above.

Generally, the electrophotographic apparatus 30 includes a photoconductor unit (e.g., an electrophotographic photoconductor drum 28,29), a charging device 25 which charges the photoconductor unit, an imagewise light irradiating device/developing device 22, 24 which irradiates the charged photoconductor unit with imagewise light to form an electrostatic latent image on the photoconductor unit and develops the electrostatic latent image with a toner to form a toner image on the photoconductor unit, and a transfer device 27 which transfers the toner image onto a receiving material, such as paper P, wherein the photoconductor unit comprises an electrophotographic photoconductor 29 as described in greater detail above. The charging device 25 may be supplied with a voltage as a charging unit and may contact and charge the electrophotographic conductor. Where desired, the apparatus may include a pre-exposure unit 23 to erase residual charge on the surface of the electrophotographic photoconductor to prepare for a next cycle.

Although a few preferred embodiments of the present invention have been shown and described, it would be appreciated by those skilled in the art that changes may be made in this embodiment without departing from the principles and spirit of the invention, the scope of which is defined in the claims and their equivalents.

What is claimed is:

1. A photoconductor for electrophotography, comprising:

a photosensitive layer that includes a charge generating material and a charge transporting material on a conductive substrate, wherein the photosensitive layer comprises at least one compound represented by the following general formula (I)

(I)

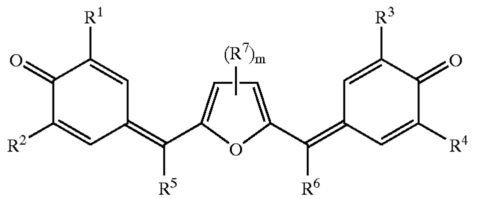

wherein each of $R^1$, $R^2$, $R^3$ and $R^4$, is independently selected from the group consisting of hydrogen atoms, alkyl groups having 1–6 carbon atoms that optionally have substituents and aryl groups that optionally have substituents, each of $R^5$ and $R^6$ is independently selected from the group consisting of hydrogen atoms, alkyl groups having 1–6 carbon atoms that optionally have substituents, aryl groups that optionally have substituents and heterocyclic groups that optionally have substituents, $R^7$ is selected from the group consisting of halogen atoms, alkyl groups having 1–6 carbon atoms that optionally have substituents, aryl groups that optionally have substituents and heterocyclic groups that optionally have substituents, m represents an integer of 0 to 2 and a plurality of $R^7$s are the same or different, the substituents being selected from a group consisting of halogen atoms, alkyl groups having 1–6 carbon atoms, alkoxy groups having 1–6 carbon atoms, aryl groups, and heterocyclic groups.

2. A quinomethane compound having a structure represented by the following general formula (I):

(I)

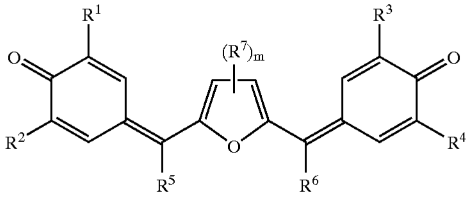

wherein each of $R^1$, $R^2$, $R^3$ and $R^4$, is independently selected from the group consisting of hydrogen atoms, alkyl groups having 1–6 carbon atoms that optionally have substituents and aryl groups that optionally have substituents, each of $R^5$ and $R^6$ is independently selected from the group consisting of hydrogen atoms, alkyl groups having 1–6 carbon atoms that optionally have substituents, aryl groups that optionally have substituents and heterocyclic groups that optionally have substituents, $R^7$ is selected from the group consisting of halogen atoms, alkyl groups having 1–6 carbon atoms that optionally have substituents, aryl groups that optionally have substituents and heterocyclic groups that optionally have substituents, m represents an integer of 0 to 2 and a plurality of $R^7$s are the same or different, the substituents being selected from a group consisting of halogen atoms, alkyl groups having 1–6 carbon atoms, alkoxy groups having 1–6 carbon atoms, aryl groups, and heterocyclic groups.

3. The photoconductor for electrophotography as claimed in claim 1, wherein the above-described photosensitive layer is a single layered photosensitive layer.

4. An electrophotographic apparatus comprising a photoconductor for electrophotography as claimed in claim 1, and carrying out a charging process by a positive charging process.

5. An electrophotographic apparatus comprising a photoconductor for electrophotography as claimed in claim 3, and carrying out a charging process by a positive charging process.

6. An electrophotographic drum comprising:

a drum; and an electrophotographic photoconductor on the drum, wherein the electrophotographic photoconductor comprises a photosensitive layer having a charge generating material and a charge transporting material on a conductive substrate, wherein the photosensitive layer comprises at least one compound represented by the following general formula (I)

(I)

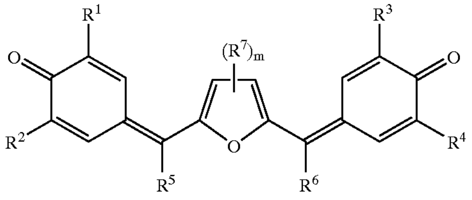

wherein each of $R^1$, $R^2$, $R^3$ and $R^4$, is independently selected from the group consisting of hydrogen atoms, alkyl groups having 1–6 carbon atoms that optionally have substituents and aryl groups that optionally have substituents, each of $R^5$ and $R^6$ is independently selected from the group consisting of hydrogen atoms, alkyl groups having 1–6 carbon atoms that optionally have substituents, aryl groups that optionally have substituents and heterocyclic groups that optionally have substituents, $R^7$ is selected from the group consisting of halogen atoms, alkyl groups having 1–6 carbon atoms that optionally have substituents, aryl groups that optionally have substituents and heterocyclic groups that optionally have substituents, m represents an integer of 0 to 2 and a plurality of $R^7$s are the same or different, the substituents being selected from a group consisting of halogen atoms, alkyl groups having 1–6 carbon atoms, alkoxy groups having 1–6 carbon atoms, aryl groups, and heterocyclic groups.

7. An electrophotographic cartridge, comprising:

an electrophotographic photoconductor that includes a photosensitive layer having a charge generating material and a charge transporting material on a conductive substrate, wherein the photosensitive layer comprises at least one compound represented by the following general formula (I)

(I)

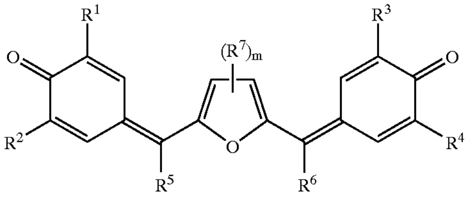

wherein each of $R^1$, $R^2$, $R^3$ and $R^4$, is independently selected from the group consisting of hydrogen atoms, alkyl groups having 1–6 carbon atoms that optionally have substituents and aryl groups that optionally have substituents, each of $R^5$ and $R^6$ is independently selected from the group consisting of hydrogen atoms, alkyl groups having 1–6 carbon atoms that optionally have substituents, aryl groups that optionally have substituents and heterocyclic groups that optionally have substituents, $R^7$ is selected from the group consisting of halogen atoms, alkyl groups having 1–6 carbon atoms that optionally have substituents, aryl groups that optionally have substituents and heterocyclic groups that optionally have substituents, m represents an integer of 0 to 2 and a plurality of $R^7$s are the same or different, the substituents being selected from a group consisting of halogen atoms, alkyl groups having 1–6 carbon atoms, alkoxy groups having 1–6 carbon atoms, aryl groups, and heterocyclic groups; and at least one of a charging device that charges the electrophotographic photoconductor;

a developing device that develops an electrostatic latent image formed on the electrophotographic photoconductor; and a cleaning device which cleans a surface of the electrophotographic photoconductor, wherein the electrophotographic cartridge is attachable to and detachable from the electrophotographic apparatus.

8. An electrophotographic apparatus comprising:

a photoconductor unit comprising an electrophotographic photoconductor that includes a photosensitive layer having a charge generating material and a charge transporting material on a conductive substrate, wherein the photosensitive layer comprises at least one compound represented by the following general formula (I)

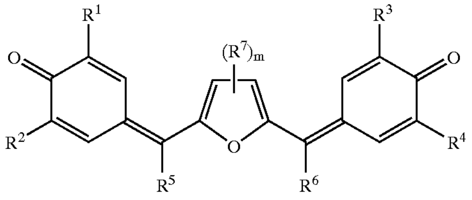

(I)

wherein each of $R^1$, $R^2$, $R^3$ and $R^4$, is independently selected from the group consisting of hydrogen atoms, alkyl groups having 1–6 carbon atoms that optionally have substituents and aryl groups that optionally have substituents, each of $R^5$ and $R^6$ is independently selected from the group consisting of hydrogen atoms, alkyl groups having 1–6 carbon atoms that optionally have substituents, aryl groups that optionally have substituents and heterocyclic groups that optionally have substituents, $R^7$ is selected from the group consisting of halogen atoms, alkyl groups having 1–6 carbon atoms that optionally have substituents, aryl groups that optionally have substituents and heterocyclic groups that optionally have substituents, m represents an integer of 0 to 2 and a plurality of $R^7$s are the same or different, the substituents being selected from a group consisting of halogen atoms, alkyl groups having 1–6 carbon atoms, alkoxy groups having 1–6 carbon atoms, aryl groups, and heterocyclic groups; and at least one of a charging device which charges the photoconductor;

an imagewise light irradiating device/developing device which irradiates the charged photoconductor unit with imagewise light to form an electrostatic latent image on the photoconductor unit and develops the electrostatic latent image with a toner to form a toner image on the photoconductor unit; and a transfer device which transfers the toner image onto a receiving material.

* * * * *

UNITED STATES PATENT AND TRADEMARK OFFICE
CERTIFICATE OF CORRECTION

PATENT NO. : 6,933,091 B2
APPLICATION NO. : 10/444094
DATED : August 23, 2005
INVENTOR(S) : Nobuyuki Sekine et al.

It is certified that error appears in the above-identified patent and that said Letters Patent is hereby corrected as shown below:

Title Page, Column 1 Item (73) (Assignee), Line 1, delete “Devices” and insert -- Device -- therefor.

Title Page, Column 2 Item (56) (Other Publications), Line 6, delete “dispersable” and insert -- dispersible -- therefor.

Signed and Sealed this

Nineteenth Day of February, 2008

JON W. DUDAS
*Director of the United States Patent and Trademark Office*